US012629536B2

(12) United States Patent
　　Reilly

(10) Patent No.:　US 12,629,536 B2
(45) Date of Patent:　May 19, 2026

(54) DEVICE FOR, AND METHOD OF, NEUROMODULATION WITH CLOSED-LOOP MICROMAGNETIC HYBRID WAVEFORMS TO RELIEVE PAIN

(71) Applicant: Quantum Nanostim LLC, Palm Harbor, FL (US)

(72) Inventor: Thomas Reilly, Treasure Island, FL (US)

( * ) Notice: Subject to any disclaimer, the term of this patent is extended or adjusted under 35 U.S.C. 154(b) by 952 days.

(21) Appl. No.: 17/818,993

(22) Filed: Aug. 11, 2022

(65) Prior Publication Data

US 2022/0387812 A1　　Dec. 8, 2022

Related U.S. Application Data

(63) Continuation-in-part of application No. PCT/US2021/017783, filed on Feb. 12, 2021.

(51) Int. Cl.
　　*A61N 2/02*　　　　(2006.01)
　　*A61N 2/00*　　　　(2006.01)
　　*A61N 2/06*　　　　(2006.01)

(52) U.S. Cl.
　　CPC ............. *A61N 2/008* (2013.01); *A61N 2/002* (2013.01); *A61N 2/006* (2013.01); *A61N 2/02* (2013.01); *A61N 2/06* (2013.01)

(58) Field of Classification Search
　　CPC .......... A61N 2/00; A61N 2/002; A61N 2/004; A61N 2/006; A61N 2/008; A61N 2/02; A61N 1/3605; A61N 1/36053; A61N 1/36057; A61N 1/3606; A61N 1/36067; A61N 1/36071
　　See application file for complete search history.

(56) References Cited

U.S. PATENT DOCUMENTS

2012/0095531 A1* 4/2012 Derbas .................... H01F 29/02
　　　　　　　　　　　　　　　　　　　　　343/866
2018/0117309 A1* 5/2018 Rapoport ............... A61B 5/686

* cited by examiner

*Primary Examiner* — Carrie R Dorna
(74) *Attorney, Agent, or Firm* — Distinct Patent Law; Justin P. Miller

(57)　　　　　　ABSTRACT

A Closed Loop Hybrid Modulation Methodology, including the following four methods of neural stimulation: METHOD 1: A priming electrical signal followed by a second magnetic signal. METHOD 2: A magnetic priming signal followed by a second electrical signal. METHOD 3: A priming magnetic signal followed by a second magnetic signal. METHOD 4: A priming hybrid electric and magnetic signal followed by a second hybrid electric and magnetic signal.

19 Claims, 17 Drawing Sheets

104

120     125     128     126     123     120     102

DEVICE FOR, AND METHOD OF, NEUROMODULATION WITH CLOSED-LOOP MICROMAGNETIC HYBRID WAVEFORMS TO RELIEVE PAIN

CROSS-REFERENCE TO RELATED APPLICATION

This application claims priority to PCT application PCT/US21/17783, filed on Feb. 12, 2021, titled Device for, and method of, neuromodulation with closed-loop micromagnetic hybrid waveforms to relieve pain, which in turn claims priority to U.S. patent application Ser. No. 62/975,811, filed on Feb. 13, 2020, titled Device for, and method of, stimulation with closed loop hybrid waveform to relieve pain.

FIELD

This disclosure relates to systems and methods for providing closed loop hybrid stimulation of neural structures, and, more specifically, for managing pain with either multiple signals or a single signal having modulated characteristics.

BACKGROUND

The term Spinal Cord Stimulation (SCS) is used to describe an advanced management therapy for chronic pain in which a varying electric field is applied to the Dorsal Columns (DC) of the spinal Cord via an electrode array (or electrode arrays) implanted in the epidural space. Conventional SCS also called "tonic," traditionally consisting of an electric field varying between 40-250 Hz that is directed to a targeted pain location by overlaying it with a perceived tingling sensation, known as paresthesia, created by the stimulating electric field. This therapy has been clinically utilized for about half a century.

The principal mode of action is based on the Gate Control Theory formulated by Melzack and Wall, although a full understanding of the mechanism has yet to be elucidated. The concept behind tonic SCS is that the paresthesia induced by the applied varying electric field masks, or "closes the gates to", pain signals travelling to the brain, however, the relationship between frequency, waveform shape, amplitude and pulse width and the mechanism by which SCS provides an analgesic effect is not fully understood.

Spinal cord stimulation (SCS) using electrical pulses has proven to decrease opioid pain medication usage as it addresses the neuropathic cause of a patient's pain. But there are significant disadvantages of electrical stimulation.

A leading barrier to traditional SCS is encapsulation of the electrodes by glial cells, referred to as "glial encapsulation" or "glial scar" caused by gliosis. This scarring typically occurs within 50-100 μm of the probe.

The scarring results in increased impedance, increased signal noise, and increased distance to the target neurons, with a net result of decreased stimulation efficacy.

As a further complication, in an attempt to maintain efficacy, the implantable pulse generator (IPG) compensates by increasing amplitude, causing a decrease in IPG lifetime.

If increases to the amplitude fail to overcome the impedance, the remaining options are a surgical revision or removal of the device, with corresponding increases in morbidity and mortality.

Given the issues with electrical stimulation, there is an interest in magnetic stimulation. Several studies have shown advantages of magnetic-based neuromodulation as compared to traditional electrical stimulation, including:

the magnetic field is not affected by glial encapsulation, depolarization of the targeted neurons can occur from a greater distance more consistently, magnetic stimulation affords high orientation specificity, increased battery life due to decreased IPG energy consumption (as opposed to traditional SCS IPG which requires compensatory increases amplitude to overcome glial encapsulation); and magnetic stimulation causes depolarization of both the extracellular matrix and intracellular matrix.

The proposed Closed-Loop Omnidirectional, Neuromodulation with Eddy currents (CLONE) would be able to overcome these anatomic and physiological obstacles.

SUMMARY

A closed loop hybrid waveform that uses two stimuli, one is a conventional tonic or burst spinal cord stimulation with an electric field varying between 40-1500 Hz and the second stimulus consisting of a continuous or varying electromagnetic field (EMF) or magnetic field (with either an electromagnet, temporary magnet, or permanent magnet) to modulate neurons, ganglions, glial cells, and promote second messengers to down-regulate the nociceptive and neuropathic pain for relieving chronic pain of the central nervous system, peripheral nervous system, sympathetic nervous system, parasympathetic nervous system.

Transcranial magnetic stimulation (TMS) is a technique to stimulate the nervous system non-invasively through the intact scalp and skin. The TMS machine delivers a short pulse of electric current into a TMS coil to generate a quick changing magnetic field surrounding the coil. TMS stimulates the neuronal circuits with the eddy current induced by the changing magnetic field, based on Faraday's law One apparatus for creating magnetic fields is a microcoil. A microcoil is a tiny electrical conductor such as a wire in the shape of a spiral or helix, which could be a solenoid or a planar structure. In the field of quantum sciences, microcoils play an increasing role for fast spin control in nanoscale devices as multi-qubit spin registers and quantum memories or for the actuation of single nuclear spins e.g. around a Nitrogen-vacancy center.

Like the coils used in TMS, when current is applied to a microcoil a magnetic field is generated. Temporal changes of the magnetic field induce the electrical field, which evokes action potentials, through eddy currents, similar to TMS.

Micro Magnetic Stimulation (μMS) uses coils. μMS can induce electric currents in the tissue from a distance (i.e., through an insulation layer).

In nature these currents are closed-loop circular currents with a higher spatial focality. Magnetic lines form continuous closed-loops because a magnetic monopole does not exist in nature. We always find magnetic poles—North and South poles which are coupled together in such a way that field lines originating from one pole end at the other loop, forming a closed-loop. Thus, magnetic field-lines behave in a different manner to electric field-lines, which begin on positive charges, end on negative charges, and never form closed-loops.

Furthermore, the fact that μMS coils can deliver stimulation while being insulated from the tissue increases their biocompatibility and compatibility with magnetic resonance imaging, so long as no ferromagnetic material is present.

The mechanisms of action of magnetic stimulation are fundamentally different from that of electrical stimulation.

Electrical stimulation activates neural elements by operating on the electric potential of the extracellular matrix and manipulating the transmembrane potentials. In contrast, eddy currents act not only upon the extracellular matrix but also on the intracellular matrix as the magnetic stimulation fields penetrate the cellular compartments.

In addition, unlike electrical stimulation, µMS does not require direct galvanic contact with the tissue. In contrast, a metal electrode implanted in the tissue may lead to an oxidation-reduction reaction at the electrode-tissue interface changing the pH of surrounding tissue which may provoke an immune response. Histopathology analysis has shown glial encapsulation, as noted above. With µMS however, it induces a current from a distance, without placing a metal in direct contact with the tissue.

Last, unlike electrical stimulation, µMS does not require a charge-balanced stimulation waveform. In electrical stimulation, charge balancing is necessary to avoid excessive charge accumulation at the neural interface, and thus undesired stimulation and electroporation. Electroporation to occurs when the external electric field of the membrane potential of the cell exceeds a 0.2-1 V threshold, which leads to a change in the molecular structure of the membrane, and a subsequent membrane perforation with pore formation increasing the membrane permeability to ions, and molecules. Electroporation with a transmembrane potential of approximately 1 V could cause necrosis, due to membrane rupture and the subsequent cytoplasmic contents leakage and ultimately cell death. In µMS, no net charge is transferred from the electrode into tissue.

The device will also have a synaptic plasticity effect. Synaptic plasticity involves several processes by which the central nervous system undergoes neural changes. Two of these mechanisms which commonly affect the efficacy of a synapse are long-term potentiation (LTP) and long-term depression (LTD). The device will also have a Metaplastic effect. Metaplasticity refers to neural changes that are induced by activity at one point in time and that persist and affect subsequently induced LTP or LTD. Metaplasticity refers to neuronal changes that are elicited at one point in time, by what is commonly called "priming" activity. By virtue of their persistence, these neuronal changes are able to regulate synaptic plasticity processes minutes, hours, or days later. A key feature of metaplasticity is that this change, can outlast the triggering ("priming") bout of activity and persists until the second bout of activity occurs to induce LTP or LTD. This effect slowly decays over time. It is also possible to convert a decaying LTP or LTD into a longer-lasting form, through plasticity-related proteins (PRP), facilitating the persistence of otherwise decaying LTP or LTD.

The device can either cause a Homosynaptic or Heterosynaptic Metaplastic effect. Homosynaptic Metaplastic affects the priming synaptic activity on plasticity mechanisms, but the effects are confined to the primed synapses. Heterosynaptic metaplasticity affects not only the activated synapses but also neighboring non-activated synapses, which can cause long-range interactions between synapses spread across dendritic compartments, in both intracellular and intercellular signaling pathways.

The closed loop system will be responsive to evoked compound action potential (ECAP) to provide feedback to adjust to the best waveform and stimulation. This closed-loop system will include adjustable parameters such as amplitude variation, and feedback parameters such as conduction velocity, rheobase, chronaxie and the occurrence of Late Response—neural response resulting from dorsal root activation.

Therefore, the device will utilize two forms of closed-loop features, the natural magnetic (North Pole to South Pole) form, as discussed above and with the feedback from ECAP's.

It may also have a gradiometer, magnetometer or both, to detect evoked magnetic fields, current sources, and record nerve conduction velocities to allow a more detailed evaluation of the neural electrical activity. It is possible that the ECAP and evoked magnetic fields may be combined to form a hybrid evoked action potential (HEAP)— both electric and magnetic—which could potentially lead to a more precise delivery charge to the target neurons, ganglions, or glial cells. These components would be embedded on a flexible silicon wafer embedded into pseudoelastic memory metal or shape memory polymer (SMP) or a combination of the two, made up of an input unit, central processing unit (memory unit, control unit, and arithmetic and logic unit), output unit, printed circuit board (PCB), connected to a multiplexer and a demultiplexer to allow for more precise stimulation and recording.

The device is a Closed Loop Omnidirectional Neuro-modulation with Eddy currents (CLONE).

Four hybrid methods will be evaluated, but the platform is not limited to these four methods.

The methods include two signals: First, a priming signal that will lower the depolarization threshold, and a second signal that will depolarize the target tissue with the lowest effective charge dose, thus improving energy efficiency of the device and lowering side effects and tissue toxicity.

In summary:

METHOD 1: A priming electrical signal followed by a second magnetic signal.

METHOD 2: A magnetic priming signal followed by a second electrical signal.

METHOD 3: A priming magnetic signal followed by a second magnetic signal.

METHOD 4: A priming hybrid electric and magnetic signal followed by a second hybrid electric and magnetic signal.

In greater detail:

METHOD 1 A closed-loop hybrid waveform that uses two stimuli, one conventional tonic or burst spinal cord stimulator with an electric field varying between 40-1500 Hz and a second stimulus in the form of a continuous or varying magnetic field to modulate neurons, ganglions, glial cells, and promote second messengers to down-regulate the nociceptive and neuropathic pain for relieving chronic pain.

METHOD 2: A closed-loop hybrid waveform that uses two stimuli, one that is a continuous or varying magnetic field and the second stimulus consisting of a conventional tonic or burst spinal cord stimulator with an electric field varying between 40-1500 Hz to modulate neurons, ganglions, glial cells, and promote second messengers to down-regulate the nociceptive and neuropathic pain for relieving chronic pain.

METHOD 3: A closed-loop hybrid waveform that uses two stimuli, one formed from a continuous or varying magnetic field and the second stimulus formed from another continuous or varying magnetic field to modulate neurons, ganglions, glial cells, and promote second messengers to down regulate the nociceptive and neuropathic pain for relieving chronic pain.

METHOD 4: A closed-loop hybrid waveform that uses two stimuli, one formed from a hybrid electric and magnetic signal and a second stimulus formed from another hybrid electric and magnetic signal to modulate neurons, ganglions, glial cells, and promote second messengers to down regulate the nociceptive and neuropathic pain for relieving chronic pain.

Methods 1, 2, 3, 4 will cause depolarization at a much lower threshold than then is currently possible.

The methods above are more effective than known methods, will not be limited by glial encapsulation and will have reduced battery usage. Both of these attributes decrease morbidity and mortality related to surgical revisions and battery replacements, respectively.

Additionally, the magnetic field can overcome glial encapsulation. One of the leading barriers to the current spinal cord stimulation systems is encapsulation of the electrodes by glial cells and fibroblasts, referred to as glial scar or glial encapsulation. The magnetic field is able to pass through the scar tissue without degradation, in contrast to traditional systems. Glial encapsulation occurs within hours after the implantation and continues indefinitely thereafter. This natural inflammatory/immune response decreases the efficacy of the treatment in several ways: A) Increasing impedance; B) Increase distance (separation) from the target neurons; and C) Decreasing implantable pulse generator (IPG) longevity, due to compensatory increase in amplitude in attempts to overcome the impedance and distance to target.

The apparatus that is used to form this hybrid wave form is preferably an array or paddle or paddle array of electrodes—referred as contacts or leads—that allows for reduction in chronic pain without being affected by glial encapsulation.

One of the advantages of this system is the ability to prolong battery life, due to small charges (nanocoulombs) being applied to the stimulator leads or arrays. Additional benefits include: A) No need to increase amplitude to overcome glial encapsulation; B) Less energy to cause an action potential, due to lower threshold caused by the priming stimulus; C) Feedback from ECAP, Evoked Magnetic Fields, and HEAP, that will prevent overstimulation, thereby using less energy overtime; and D) unidirectional stimulation, also requires less energy.

Disclosed herein is an apparatus and methods for managing pain in a patient by using closed-loop hybrid stimulation of neural structures, with either multiple signals or a single signal having modulated characteristics. Hybrid modulation for pain management, in accordance with the disclosure, contemplates the use of multiple separate varying stimuluses which are independently applied via an array of electrodes (referred as contacts or leads) to a particular neural structure using a variety of temporal and amplitude characteristics, to modulate chronic pain without being affected by glial encapsulation. Specifically, disclosed is an apparatus and method for modulating the expression of the neurovasculature of the spine and second messengers involved in diverse pathways including inflammatory/immune system mediators, ion channels and neurotransmitters, in both the Spinal Cord (SC) and Dorsal Root Ganglion (DRG). In one embodiment, such expression modulation is caused by spinal cord stimulation or peripheral nerve stimulation. In one embodiment, the amplitudes and frequencies of the signal or signals used to create the hybrid stimulation of neural structures may be optimized for improved pain relief with minimal power usage in an IPG, as described herein.

In one embodiment of hybrid modulation therapy, the tonic or burst signal may be either monophasic, or biphasic, with the polarity being either cathodic or anodic. In another embodiment the hybrid wave form may include one stimulus, either EMF, magnetic, or tonic or burst.

Turning to the physical device, the collapsible nerve stimulator has two primary states: a long and narrow profile for insertion, and a wider, expanded profile for operation.

The result is a large surface area is available for nerve stimulation but the need for a large incision is avoided.

The implantation process is summarized as follows:

A needle is inserted into the epidural space.

A guidewire is then inserted to the target location

The device with a sheath is loaded over the guidewire.

When the head of the device is in the desired location, the sheath of the device is drawn back, allowing the sections of the lead near the tip to expand;

The device may also have an internal tensioning cable, thus allowing the distal end of the paddle lead to retract or deploy;

This process is reversible if the device needs to be repositioned, or removed entirely;

The needle is then removed, and then distal portion of the array is connected to the IPG.

Turning to stimulation devices generally, there are two primary types: paddle leads (flat) and percutaneous leads (cylindrical or isodiametric).

Paddle leads are surgically implanted because they are wider than percutaneous arrays, and are placed in a retrograde manner, due to anatomical constrains. This makes implantation of a paddle array using a needle a technical conundrum.

The flat and wide profile of a paddle lead results in physical stability. Generally, a paddle lead only includes electrodes on a single side, which is place facing the nerve to be stimulated. This directed stimulation conserves power—critical in a device powered by batteries.

Percutaneous or cylindrical leads are implanted through a needle. Thus, a round profile is common for compatibility with the needle. Implantation is simplified by the use of the needle as compared to surgical implantation.

But the simplicity of implantation is offset by decreased physical stability and circumferential stimulation, which draws additional power.

The collapsible neural stimulator is insertable in the manner of a lead, but once in position, can be expanded into the shape of a paddle.

The components include an array/lead housed inside a sheath. The collapsible neural stimulator is passed over a guide wire, which is later withdrawn.

As the sheath is withdrawn, the lead is able to expand in width within the body.

The material of the expanding lead is preferably a biological compatible material—such as pseudoelastic memory metal or shape memory polymer (SMP) or a combination of the two—that when warmed by the body seeks to conforms to the neural structure for stimulation or recording.

Electrodes are placed on the folding sections of the lead, and optionally on the body of the lead. The electrodes are anticipated to include between four and sixty-four points.

With the anticipated placement of two identical arrays in adjacent positions, this results in a total of eight to one hundred and twenty-eight contact points.

During use, the device must be powered. Multiple sources of power exist. A battery is optionally placed within the body, using chemical energy converted to electrical energy to power the device.

As a further alternative, an internal generator recharges the battery, converting motion of the user into electrical power.

This generator, referred to as a nanogenerator due to its small size, may work in multiple ways. For example, piezoelectric, triboelectric, or pyroelectric. The piezoelectric and triboelectric nanogenerators convert mechanical energy into electricity. Pyroelectric nanogenerators can convert thermal energy into mechanical energy.

As mechanical energy surrounding us is available, transduction mechanisms based on electromagnetic, piezoelectric, electrostatic, and triboelectric principles are available to convert mechanical energy into electric energy.

Turning to the methodology of stimulation, specifically Closed Loop Hybrid Modulation Methodology:

The priming electrical signal lowers the threshold for depolarization of nerve fibers while simultaneously modulating neurons, ganglions, glial cells. The priming electrical signal also lowers the impedance of the stimulated tissue, which allows for better penetration of the electric field into the neural tissue. The frequent pulsing of the priming electrical signal also contributes to a lower threshold for depolarization of nerve fibers via membrane integration of the electrical or EMF or magnetic stimulus. Additionally, the priming electrical signal contributes to neuronal desynchronization, which is a mechanism that helps with the reestablishment of neuronal circuits that have been unnaturally synchronized to maintain a nociceptive input into the brain. The plurality of electrodes permits varying stimulation of the targeted area. That is, one or more of the electrodes on the array bodies transmit the stimulation pulses to targeted tissue depending on the desired stimulation in accordance with the measured ECAP, evoked magnetic field, or HEAP. The hybrid system may run on alternating current, direct current, or both.

In a first embodiment, the device stimulates or modulates the interaction between neurons and ganglions of a subject by: A) exposing neurons, ganglions, and glial cells of the subject to a first stimulus; and B) simultaneously exposing the neurons, ganglions, and glial cells of the subject to a second stimulus; wherein the first stimulus and the second stimulus have at least one uncommon parameter amongst them. In one embodiment, the first stimulus is composed of constant or varying electrical signal and the second stimulus is a varying or constant EMF. In another embodiment, the aforementioned stimulations may have different values for frequency, amplitude, phase polarity, relative phase, harmonic content, or width for sinusoidal or rectangular waveforms.

In a second embodiment, the device stimulates or modulates the interaction between neurons, ganglions, and glial cells of a subject by: A) exposing neurons, ganglions, glial cells of the subject to a first stimulus or signal; and B) simultaneously exposing the neurons, ganglions, and glial cells of the subject to a second stimulus or signal; wherein the first stimulus and the second stimulus have at least one uncommon parameter amongst them. In one embodiment, the first stimulus is composed of varying or constant EMF and the second stimulus is a constant or varying electrical signal. In another embodiment, the aforementioned stimulations may have different values for frequency, amplitude, phase polarity, relative phase, harmonic content, or width for sinusoidal or rectangular waveforms.

In a third embodiment, the device stimulates or modulates the interaction between neurons, ganglions, glial cells of a subject by: A) exposing neurons, ganglions, and glial cells of the subject to a first stimulus; and B) exposing the neurons, ganglions, and glial cells of the subject to a second stimulus; wherein the first stimulus and the second stimulus have a common parameter amongst them. In one embodiment, the first stimulus comprises a first varying or constant EMF and the second stimulus to comprises of a varying or constant EMF. In another embodiment, the first varying or constant EMF and second varying or constant EMF are provided by a composite electrical stimulation. In still another embodiment, the composite electrical stimulation may be any frequency, amplitude, phase polarity, relative phase, harmonic content, or width for sinusoidal or rectangular waveforms.

In a fourth embodiment, the device stimulates or modulates the interaction between neurons, ganglions, glial cells of a subject by: A) providing lead arrays having a plurality of electrode contacts electrically attached to an electrical stimulation source; B) electrically coupling a first subgroup of the plurality of electrode contacts to a first electrical stimulation or EMF source; C) electrically coupling a second subgroup of the plurality of electrode contacts to a second electrical stimulation or EMF source; D) exposing neurons, ganglions, and glial cells of the subject to the first electrical stimulation or EMF from the first subgroup of electrode contacts; and E) simultaneously exposing the neurons, ganglions, and glial cells of the subject to the electrical stimulation or EMF from the second subgroup of electrode contacts.

In a fifth embodiment, the device modulates pain in a subject comprising activating neurons and ganglions by regulating any of the second messengers for calcium binding proteins, cytokines, cell adhesion or specific immune response proteins. A) Lowering a threshold for depolarization of nerve fibers in the subject with a first electrical stimulation or EMF for a first period of time; and B) simultaneously modulating neurons and ganglions with a second varying electrical stimulation or EMF during a second period of time not identical to the first period of time causing down-regulation of nociceptive and neuropathic pain.

In a sixth embodiment, the method for managing pain in a subject includes: A) lowering a threshold for depolarization of nerve fibers in the subject with a first varying electrical stimulation or EMF for a first period of time; and B) simultaneously modulating second messenger activity with a second varying electrical stimulation or EMF during a second period of time not identical to the first period of time causing down regulation of the nociceptive and neuropathic pain.

In a seventh embodiment, the method for managing pain in a subject includes: A) lowering a threshold for depolarization of nerve fibers in the subject with a first varying electrical stimulation or EMF for a first period of time; and B) simultaneously modulating neurons, ganglion, and glial cells activity with a second varying or constant EMF during a second period of time not identical to the first period of time; wherein the first varying electrical stimulation or EMF is provided by an electric signal having an amplitude set to a value corresponding to a percentage of a Priming Threshold of the subject, and wherein a second varying or constant EMF is provided by an electric signal having an amplitude set to a value corresponding to a percentage of the paresthesia threshold (PT).

In one embodiment of hybrid modulation therapy, the priming signal may be monophasic, or biphasic, in which the polarity of the first phase of the biphasic priming signal may be either cathodic or anodic. With this embodiment, the tonic or burst signal may have waveform characteristics that are different from those of the priming signal. The tonic or burst signal may be either monophasic, or biphasic, with the polarity of the first phase of the biphasic tonic or burst signal being either cathodic or anodic.

In a seventh embodiment, a method for stimulating/ modulating the interaction between neurons and ganglions of a subject includes: A) exposing neurons, ganglions, and glial cells of the subject to a first stimulus; and B) simultaneously exposing the neurons, ganglions, and glial cells of the subject to a second stimulus; wherein the first stimulus and the second stimulus have different respective phase polarities. In one embodiment, the first stimulus and the second stimulus comprise electrical stimulations or EMF. In another embodiment, the electrical stimulations or EMF have different values for any of their respective frequency, amplitude, waveform shape, or width in the case of sinusoidal or rectangular waveforms.

In an eighth embodiment, a method for stimulating and modulating the interaction between neurons, ganglions, and glial cells of a subject includes: A) providing lead arrays having a plurality of electrode contacts electrically coupleable to an electrical stimulation source; B) electrically coupling a first subgroup of the plurality of electrode contacts to a first electrical stimulation or EMF source; C) electrically coupling a second subgroup of the plurality of electrode contacts to a second electrical stimulation or EMF source; D) exposing neurons and ganglions of the subject to the first electrical stimulation or EMF from the first subgroup of electrode contacts; and E) simultaneously exposing the neurons, ganglions, and glial cells of the subject to the second electrical stimulation or EMF from the second subgroup of electrode contacts wherein the first electrical stimulation or EMF and the second electrical stimulation or EMF have different respective phase characteristics.

In a ninth embodiment, the method for managing pain in a subject includes: A) lowering a threshold for depolarization of nerve fibers in the subject with a first varying electrical stimulation or EMF; and B) simultaneously modulating neurons, ganglions, and glial cells with a second varying electrical stimulation or EMF. In one embodiment, the first varying stimulus and the second stimulus have any of different respective frequencies, amplitudes, phases, harmonic content, or width for rectangular waveforms. In another embodiment, the first and second varying electromagnetic fields may be provided by either a single electrical stimulation or EMF or by two different electrical stimulations or EMF's.

In a tenth embodiment, a system is provided comprising a signal generation module and one or more leads. The leads are configured for exposing neurons, ganglions, and glial cells simultaneously to a first electrical stimulation or EMF and a second electrical stimulation or EMF. The signal generation module is configured for having an operating mode for providing a first and a second electric signal having at least one common parameter amongst them or at least one uncommon parameter amongst them to the one or more leads.

Also disclosed herein is an apparatus comprising a signal generation module that is configured for electrically coupling with one or more leads. In addition, the leads will be able to capture ECAPs, evoked magnetic fields, or HEAP to improve charge delivery to spinal targets. Coupling of the apparatus with one or more leads may provide the system.

Optionally, the signal generation module comprises at least a first and a second electric signal source or terminal and the one or more leads comprise at least a first and a second subgroup of electrodes. The first subgroup of electrodes can be electrically coupled to the first electric signal source and/or terminal and the second subgroup of electrodes can be electrically coupled to the second electric signal source and/or terminal.

Optionally, the signal generation module is configured for having an operating mode for providing at least first and second electric signals or EMF's corresponding to the first and second electrical stimulation or EMF as described herein. Optionally, the first and second electric signals or EMFs have a different frequency.

Optionally, the signal generation module is configured for having an operating mode for providing electric signals to the electrodes corresponding to the electrical stimulation or EMF stimulus of any of the methods described herein.

Other parameters of the first and second electric signals may be different, such as the pulse width and/or amplitude. The first electric signal can be fired synchronously, i.e., simultaneously, with the second electric field, or asynchronously, i.e., with a given time delay relative to the first electric signal.

Optionally, the signal generation module is arranged for generating a composite electric signal or EMF. The composite electric signal can be a summed signal of the first and second electric signals or EMF. Optionally, the signal generation module is arranged for generating a hybrid signal, such as a frequency-modulated signal, amplitude modulated signal, harmonic modulated signal. The composite signal and/or the hybrid signal can be provided to the one or more leads.

Optionally, the signal generation module comprises two or more electric signal sources or EMF, such as signal generators, that are independently controllable, and are configured for delivering electric signals or EMF with parameters that can be set separately for each of the electric signal sources.

Optionally, the apparatus is a not permanently implantable—for use when running a trial with a patent—the system comprising a signal generation module comprising at least two signal generators configured for delivering electric signals or EMF with parameters that can be set separately for each of the signal generators, for example a priming/tonic/burst signal and an EMF signal.

Optionally, an implantable hybrid generator is provided, that is adapted for electrically coupling with one or more leads, or optionally is coupled with one or more leads. The implantable hybrid generator comprises generator circuitry and a housing. The housing can hermetically seal the generator circuitry and can be made of a durable biocompatible material. The generator has an output interface for establishing electrical connection with electrodes implemented in one or more leads, e.g., a first and second terminal for electrically coupling to a first and second subgroup of electrodes implemented on one or more leads.

Optionally the implantable hybrid generator comprises two or more signal generators and timer electronic circuitry that can slave one of the signal generators to another signal generator, such that a delay can be produced between signals generated from the at least two signal generators.

In an eleventh embodiment, an EMF device is provided including an output unit for connection to at least one electrode array, or a plurality of arrays of electrodes, and a signal generator, wherein the stimulation device is arranged for providing a hybrid stimulation signal to at least one electrode array, or a plurality of arrays of electrodes via the output unit. The hybrid stimulation signal can be an EMF. At least one electrode array is configured for exposing neurons and ganglions to the hybrid stimulation signal. The electromagnetic stimulation device can be a pain treatment device.

Optionally, the EMF device may have an output unit that includes a first output for connection to a first lead and a second output for connection to a second lead. The first lead can include a first array of electrodes. The second lead can include a second array of electrodes.

Optionally, the signal generator is arranged for providing a first electric signal or EMF to the first output and a second electric signal or EMF to the second output. The first electric signal or EMF and the second electric signal or EMF can differ in a parameter such as amplitude, frequency, phase, phase polarity, waveform shape, and width. The first electric signal or EMF and the second electric signal or EMF may correspond in a parameter such as amplitude, frequency, phase, phase polarity, waveform shape, and width. The second electric signal or EMF can be a tonic or burst stimulation signal, and the first electric signal or EMF can have a frequency higher than the frequency of the tonic or burst stimulation signal.

Optionally, the signal generator is arranged for generating a hybrid electric signal, such as a frequency modulated signal, amplitude modulated signal, harmonic modulated signal. The hybrid electric signal can be provided to at least one electrode.

In a twelfth embodiment, a method for operating a signal generation module is provided. The method includes connecting the signal generation module to one or more leads. The leads can already have been implanted into the body of a subject. The method includes generating, using the signal generation module, a first electric signal or varying EMF at least one of the one or more leads and generating, using the signal generation module, a second electric signal or varying EMF at least one of the one or more leads. The first electric signal or varying EMF and the second electric signal or varying EMF can have at least one uncommon parameter amongst them.

In a thirteenth embodiment, an electrically conducting material is provided, such as a metal, e.g., in the form of an electrode, for use in administering an EMF into a subject for the treatment of pain. The EMF can include a first electromagnetic stimulus and a second EMF. The first stimulus and the second stimulus may have at least one uncommon parameter amongst them. The first stimulus and the second stimulus can be signals, or a composite signal, or hybrid signal as described herein.

In an fourteenth embodiment, an EMF system is disclosed with a memory for storing a plurality of hybrid signal parameter programs; a selection device for selecting one of the plurality of hybrid signal parameter programs; a hybrid signal generator controllable by a selected of the plurality of hybrid signal parameter programs; and an output unit for connection to at least one electrode; wherein the stimulation device is configured to provide a hybrid stimulation signal generated by the hybrid signal generator in accordance with a selected of the hybrid signal parameter programs to the at least one electrode via the output unit. The system may further comprise an enclosure of biocompatible material surrounding the hybrid signal generator and output unit. In one embodiment, the hybrid signal generator generates a first and second electric signals or EMF's on in an operational mode thereof. In one embodiment, the system may be combined with at least one electrode comprising at least a first and a second subgroup of electrodes, and wherein the first subgroup of electrodes is electrically coupled to the first electric signal and the second subgroup of electrodes is electrically coupled to the second electric signal or EMF.

In a fifteenth embodiment, a collapsible nerve stimulator is disclosed with two primary states: a long and narrow profile for insertion, and a wider (paddle lead), expanded profile for operation. Two arrays, with anywhere from 2 to 64 lead contacts or more. Dynamic change will result in paddle lead with anywhere between 4 to 128 contacts or more. The plurality of electrodes permits varying stimulation of the targeted area. That is, one or more of the electrodes on the lead bodies transmit the stimulation pulses to targeted human tissue depending on the desired stimulation in accordance with the measured ECAP, evoked magnetic field, or HEAP.

The bonding of the percutaneous lead bodies is accomplished by a plurality of pseudoelastic memory metal or shape memory polymer (SMP) bridges, molded to each of the percutaneous arrays, by the process of photolithography. The plurality of bridges provides structural integrity to the array yet permits the desired flexibility of the lead body. The array is housed in a sheath and has a guidewire. Once the sheath is retracted the array has an expandable region to allow the electrode array to form into a paddle lead. This process is reversible if the device needs to be repositioned or removed entirely. A method of deploying and securing the electrode is described. The tip of the array may have a circular, elliptical, parabolic, or hyperbolic opening for the guidewire. The plurality of elongate members is a plurality of leads, and the leads are fixedly secured to one another where the leads intersect with one another. The plurality of elongate members is a plurality of a pseudoelastic memory metal or polymer that when exposed to body temperature, allows it to conform to the underlying neural structure when introduced into the body. The paddle array may or may not have an insulation material that would allow for unidirectional stimulation, however it may not, which would allow for circumferential stimulation.

In another embodiment, a planar coil that provides magnetic flux which creates a modulating effect on the interaction between neurons, ganglions, and glial cells. The planar coil is coil can be between 2 to 1,000,000 turns. The planar coil can be stacked on top of itself to provide and additive effect, producing greater flux. The shape of the planar coil can be circular, elliptical, oval, parabolic, or hyperbolic shape. It can also be in the shape of a triangle, square, rectangle, rhomboid, parallelogram, trapezoid, pentagon, hexagon, heptagon, octagon, nonagon, and decagon. The turns can either be in a clockwise, counter-clockwise fashion or both.

A cylindrical coil that provides magnetic flux which creates a modulating effect on the interaction between neurons, ganglions, and glial cells. The cylindrical coil is coil can be between 2 to 1,000,000 turns. The planar coil can be stacked on top of itself to provide and additive effect, producing greater flux. The shape of the planar coil can be circular, elliptical, oval, parabolic, hyperbolic shape, or a mixture of them. It can also be in the shape of a triangle, square, rectangle, rhomboid, parallelogram, trapezoid, pentagon, hexagon, heptagon, octagon, nonagon, decagon, or a mixture of them. The turns can either be in a clockwise, counter-clockwise fashion or both.

During use, the device must be powered. Multiple sources of power exist. A battery is optionally placed outside the body or within the body, using chemical energy converted to electrical energy to power the device. Power may also be provided wirelessly. This may be accomplished using coupled radio-frequency antennas, acoustic transducers, optogenetics, or optoelectronics.

As a further alternative, an internal generator recharges the battery, converting kinetic energy into electrical power.

This generator, referred to as a nanogenerator due to its small size, may work in multiple ways. For example, piezo-electric, triboelectric, or pyroelectric. The piezoelectric and triboelectric nanogenerators convert mechanical energy into electricity. Pyroelectric nanogenerators can convert thermal energy into mechanical energy.

In another embodiment, the nanogenerator may be able to be incorporated into the array, thereby negating the necessity of an IPG.

In another embodiment the aforementioned device may be used in spinal cord injury (SCI) patients, by helping the mesenchymal stem cells, exosomes, and second messengers migrate to the target area of injury via 40 Hz EMF fre-quency.

In another embodiment, the device may include utilize Endoscopic ultrasound. This will enable 3-dimensional imaging of the target tissue, for the intervention or surgery. This map will be incorporated into the software programing of the device. This is not the current standard of care.

The ACTIVE system=Adaptive, Computational, Tomo-graphic Map, Image Overlay (3D), Vector Overlay, with Epidural ultrasound.

The ADAPTIVE=Artificial Intelligence, Definition, Adaptive, Pacing, Tomographic Map, Image (3D), Vector, with Epidural ultrasound.

In another embodiment, cylindrical coil is housed in a circular disc, on the device, which rotates between 0 to 360 degrees, thus allowing the device to steer the electrical or eddy currents providing a neuromodulation effect between neurons—the neurons including nociceptors and neuro-pathic pain—ganglions, neurovasculature, and glial cells. The rotating disc may rely on the 3D software program with epidural ultrasound above, as well as postoperative imaging or both.

In another embodiment, the planar coil is housed in a circular disc, on the device, that tilts on one axis or several axes, thus allowing the device to steer the electrical or eddy currents providing a neuromodulation effect between neu-rons—the neurons including nociceptors and neuropathic pain—ganglions, neurovasculature, and glial cells. The tilt-ing disc may rely on the 3D software program with epidural ultrasound above, as well as postoperative imaging or both.

In another embodiment the ultrasound may be used to provide neuromodulation to alleviate pain as such, Focused Ultrasound (FUS), through amplitude modula-tion creates a neuromodulation effect on the interaction between neurons, ganglions, and glial cells of the central nervous system, peripheral nervous system, sympathetic nervous system, parasympathetic nervous system. FUS between 1-20 megahertz. FUS provides an inhibitory effect at low intensities (increased firing of inhibitory interneu-rons), while providing an excitatory effect at high intensities (increased firing rate of excitatory neurons).

In another embodiment the device may be use for Deep Brain Stimulation (DBS), Tumor treating fields (TTF) for cancer, Vagus Nerve Stimulation (for Epliepsy and Arrhymias), Cardiac Dromotrophy (Ventricular arrhyth-mias, Atrial arrhythmias, Heart Failure, Sick Sinus Syn-drome, Syncope/positional orthostatic tachycardia (POTS), Heart Transplantation), Sleep apnea, Peripheral nerve stimu-lation, Spinal Cord Injury (using 40 Hz stimulation to cause migration of the Stem Cells to their target), Bioelectronics for prosthesis, Diaphragmatic Pacers.

In another embodiment the device may have a fiber optic endoscope to allow for real time footage of the intervention or procedure. This is not the current standard of care.

In another embodiment, two full-circle annular electrodes (inner and to outer) are placed inside or outside of a planar or spiral coil to line up the electric and magnetic field peaks as a means to create closer tolerance.

The outer annular electrode is segmented into between 2 (two) and 64 (sixty-four) doublets for a total of 1-32 "pairs" that act as either an anode or cathode as a means to steer the electrical current to the magnetic field peak. The timing of the electric field and magnetic field pulses must coincide such that the combined effect of each sub-threshold pulse as a means to trigger an action potential. The optimum timing of the magnetic field pulse is late in the 'charge-up' phase of the node of Ranvier at which the 'activating function' of the electric field is maximal.

The "pairs" have the same surface area as the inner electrode as a means for the anode and cathode to be charged balanced. The "pairs" can also have a different surface area, by applying the same current to achieve charge-balancing, which will yield different surface charge densities at the anode and cathode as a means to make the inner annular electrode smaller. The higher surface charge density of the smaller surface area electrode can be restricted to not exceed a given desired or safety maximum, such as 30 µC/cm2.

The electrical peaks between two annular electrodes (in-ner and outer) are further divided into a circular peak between the two electrodes, rather than a single linear peak with a linear electrode array; in a slice plot, the circular peak appears as three electrical peaks, providing a superior means to achieve more precise steering to coincide the electric field and magnetic field peaks.

It will be appreciated that any of the aspects, features and options described in view of the methods apply equally to the system, signal generation module and stimulation device. It will be understood that any one or more of the above aspects, features and options as described herein can be combined.

BRIEF DESCRIPTION OF THE DRAWINGS

The invention can be best understood by those having ordinary skill in the art by reference to the following detailed description when considered in conjunction with the accom-panying drawings in which.

BEST MODE FOR CARRYING OUT THE INVENTION

Figures 1A, 1B:
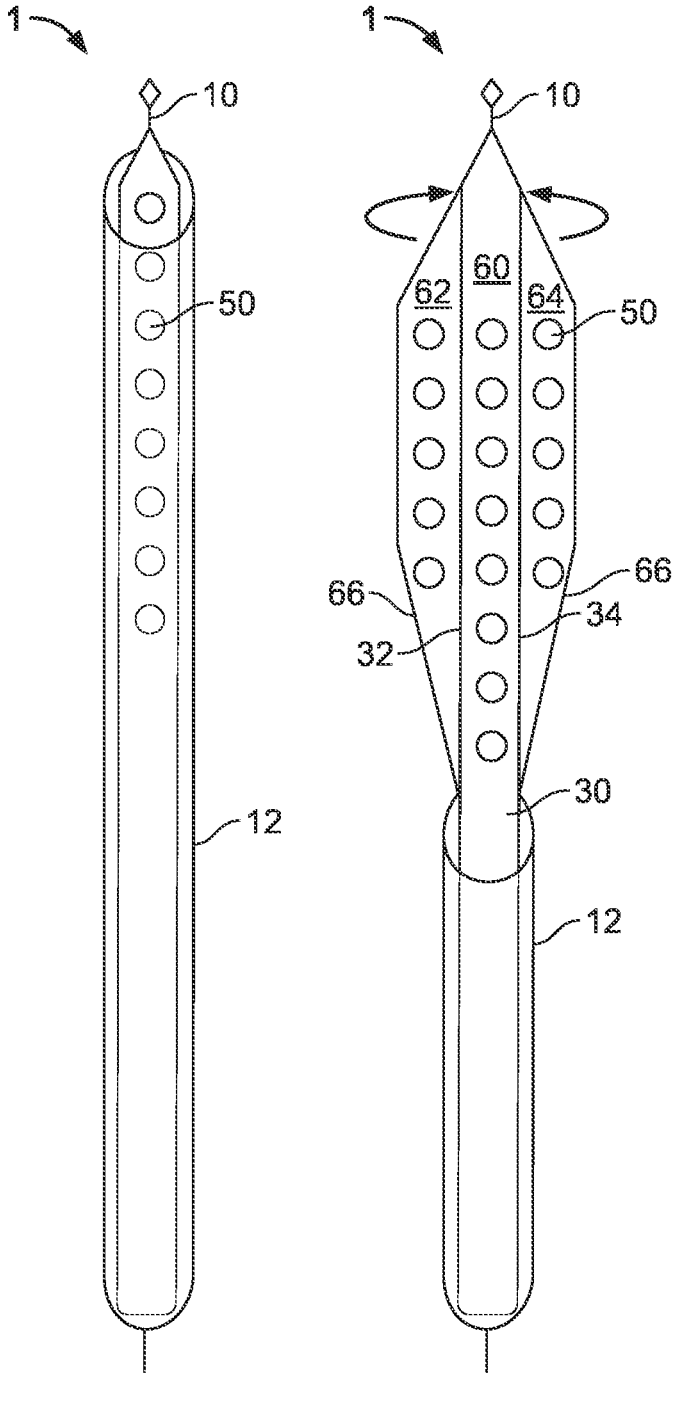
FIG. 1A illustrates a view of a cylindrical (isodiametric) embodiment of the collapsible neural stimulator.
FIG. 1B illustrates a view of insertion of the collapsible neural stimulator that expands increasing in width.

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

The techniques disclosed herein may be achieved with minimally invasive procedures which are preferred over those that require extensive surgical intervention and healthcare expenses although in particular circumstances, a surgical implantation may be required. In an embodiment, a lead comprises a cylindrical arrangement of multiple electrodes, e.g., between 2 and 64. The diameter of the lead may be small enough to allow for percutaneous implantation into the spinal canal using an epidural needle under standard clinical practice. The electrodes are made of biocompatible materials such as titanium nitride, boron-doped diamond (BDD), poly(3,4-ethylenedioxythiophene (PEDOT), thiol-ene acrylate polymers, Silicon Carbide, platinum-iridium alloys, which are also resistant to corrosion. For example, a 50 cm long lead implemented with eight electrodes may have a diameter of 1.35 mm, with each cylindrical (isodiametric) electrode having a length of 3.0 mm, and a spacing between electrodes of 4.0 mm. Conducting wires may run from the electrodes to the distal part of the lead into metal connectors. The wires may be enclosed within a triple-insulated containment made of a biocompatible material, such as a pseudoelastic memory metal or SMP.

Reference will now be made in detail to the presently preferred embodiments of the invention, examples of which are illustrated in the accompanying drawings. Throughout the following detailed description, the same reference numerals refer to the same elements in all figures.

Referring to FIGS. 1A and 1B, a view of a cylindrical (isodiametric) embodiment of the collapsible neural stimulator is shown.

Figure 2:
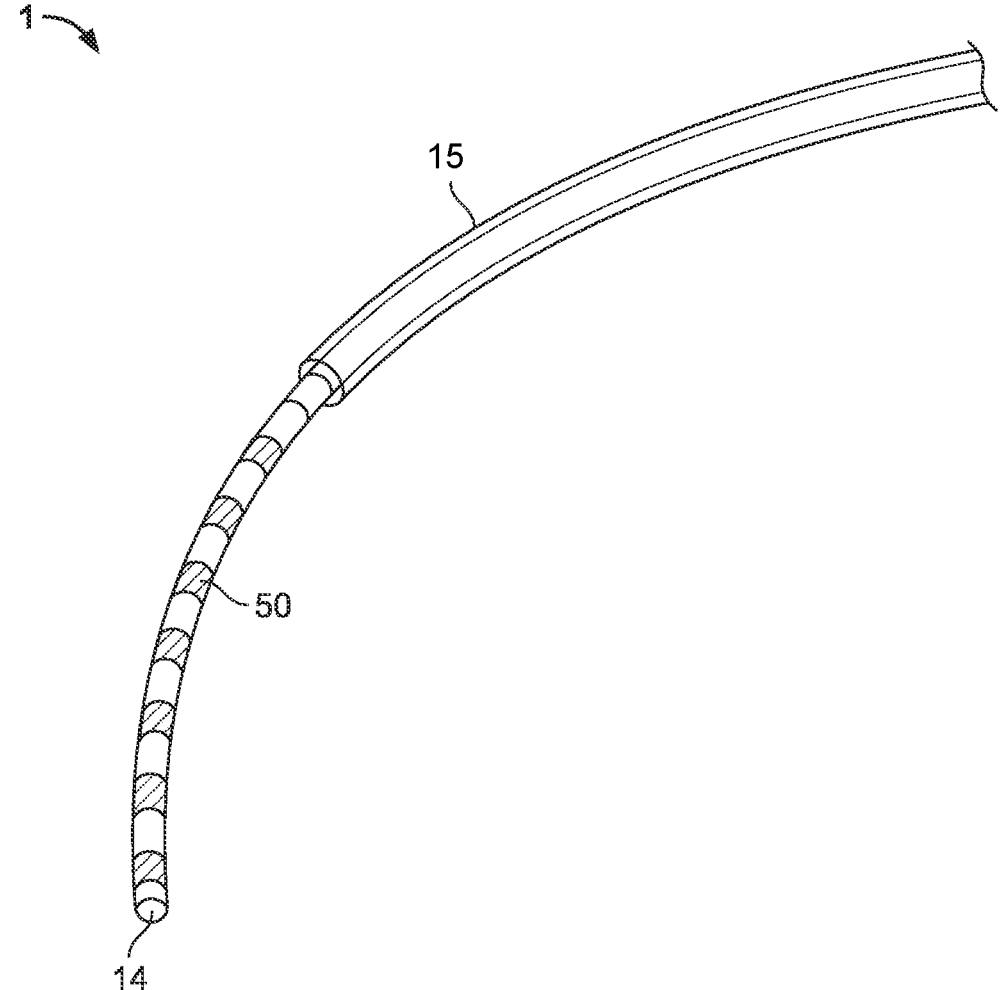
FIG. 2 illustrates a view of a cylindrical (isodiametric) neural stimulator.

The collapsible neural stimulator 1 includes a guide wire 10, a sheath 12 with electrodes 50 placed along the lead 14 (see FIG. 2).

The body 30 folds along the first hinge 32 and the second hinge 34.

The collapsible neural stimulator 1 is formed from a main section 60, with first arm 62, second arm 64, and folding ramp 66.

Referring to FIG. 2, a view of insertion of the collapsible neural stimulator is shown.

The collapsible neural stimulator 1 is inserted percutaneously through the epidural space between the vertebrae 206 (see FIG. 2). A guide tube 15 directs the lead 14 between vertebrae T12 and L1 (see FIG. 2). This insertion point is only shown by way of example.

Figure 3:
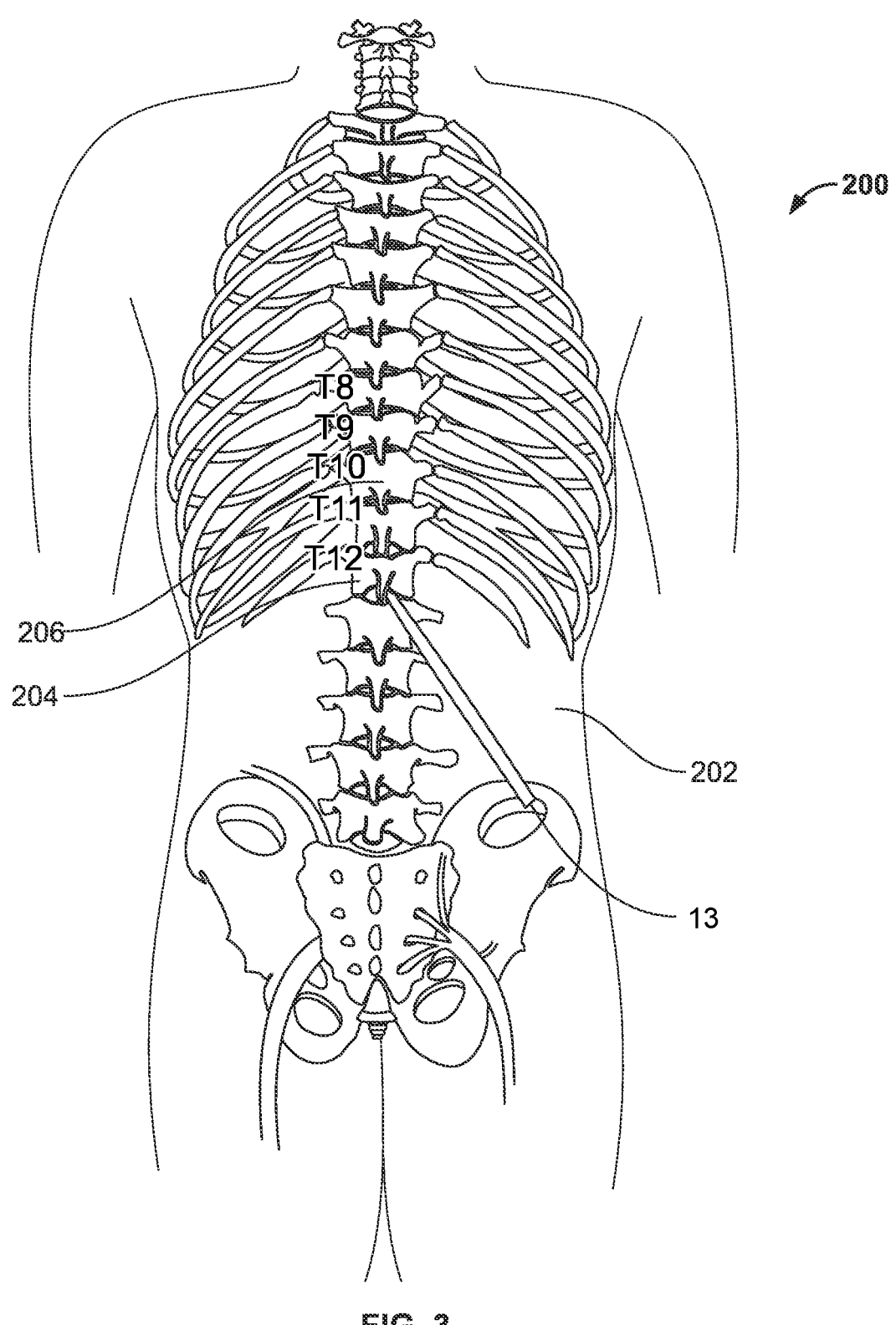
FIG. 3 illustrates an anatomical view of insertion of the collapsible neural stimulator.
Figure 4:
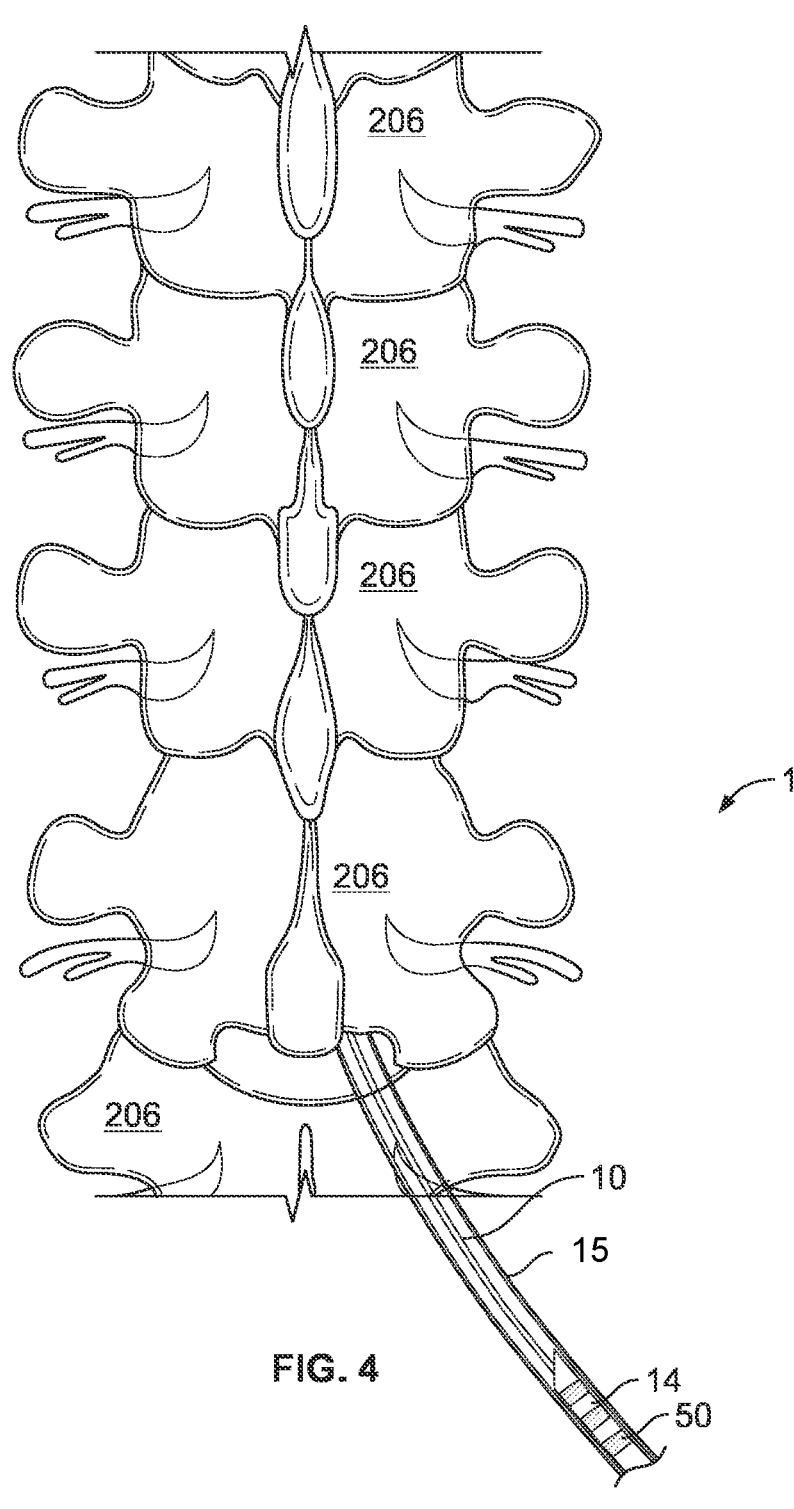
FIG. 4 illustrates a close-up view of insertion of the collapsible neural stimulator.

Referring to FIGS. 3 and 4, an anatomical view and a close-up view of insertion of the collapsible neural stimulator are shown.

The collapsible neural stimulator 1 is inserted into the patient 200, through the skin 202 and into the spine 204, between the vertebral foramen 206 using a percutaneous epidural approach, placement guided by use of a spinal needle 13.

The lead 14 passes over a guidewire 10 and within a guide tube 15 until in position.

Figure 5:
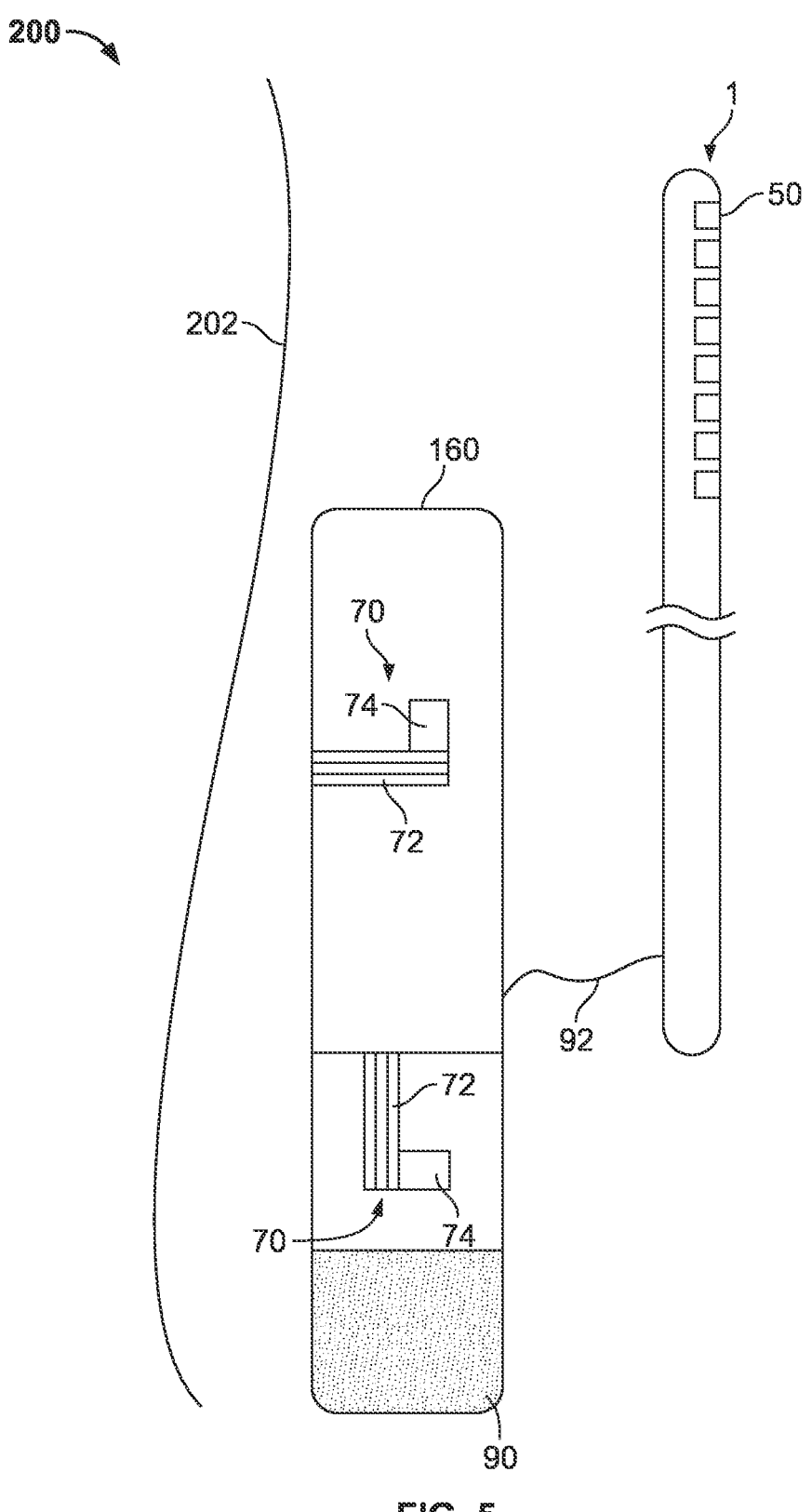
FIG. 5 illustrates a schematic view of a first means of powering of the collapsible neural stimulator.
Figure 6:
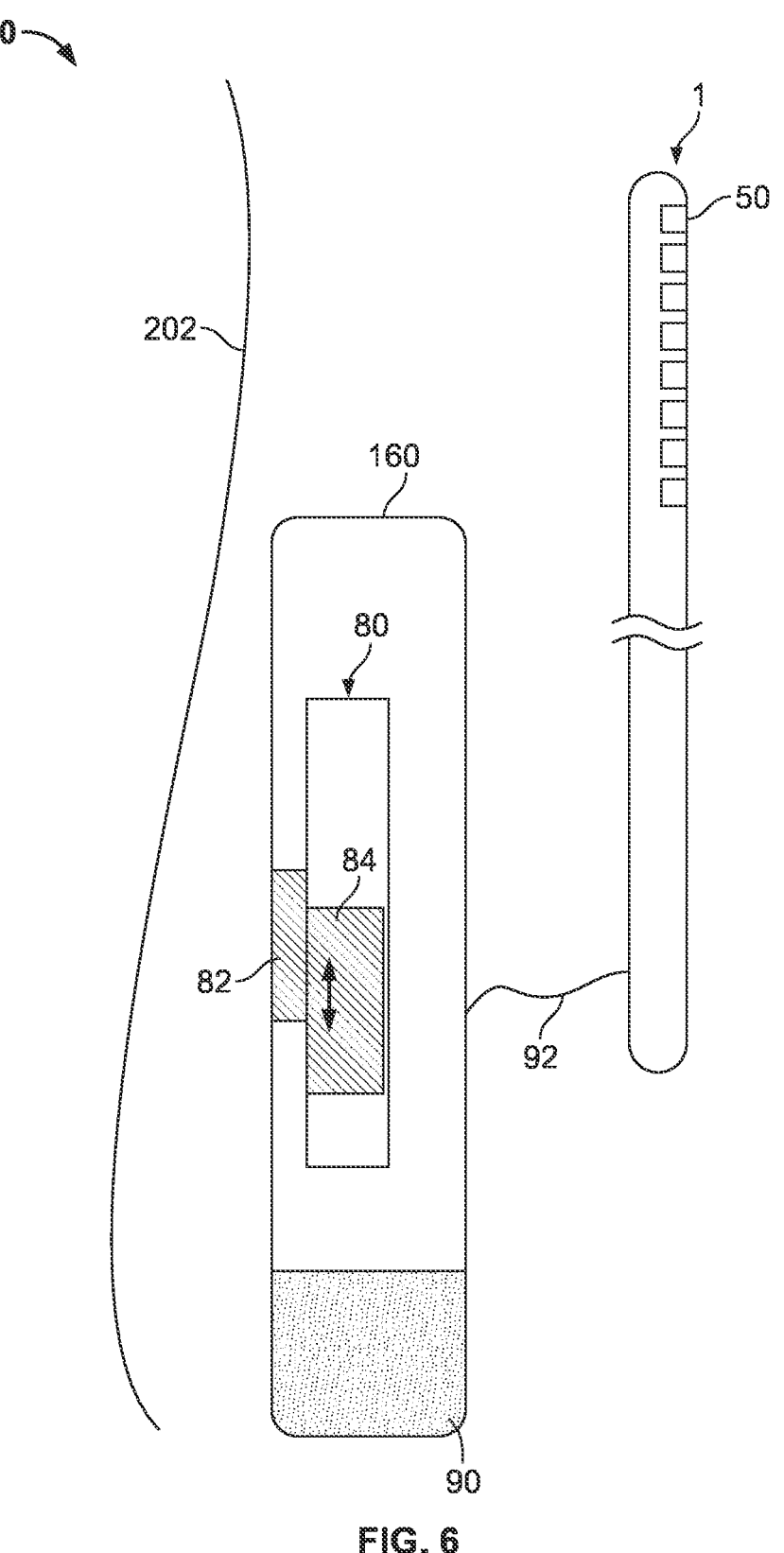
FIG. 6 illustrates a schematic view of a second means of powering of the collapsible neural stimulator.
Figure 7:
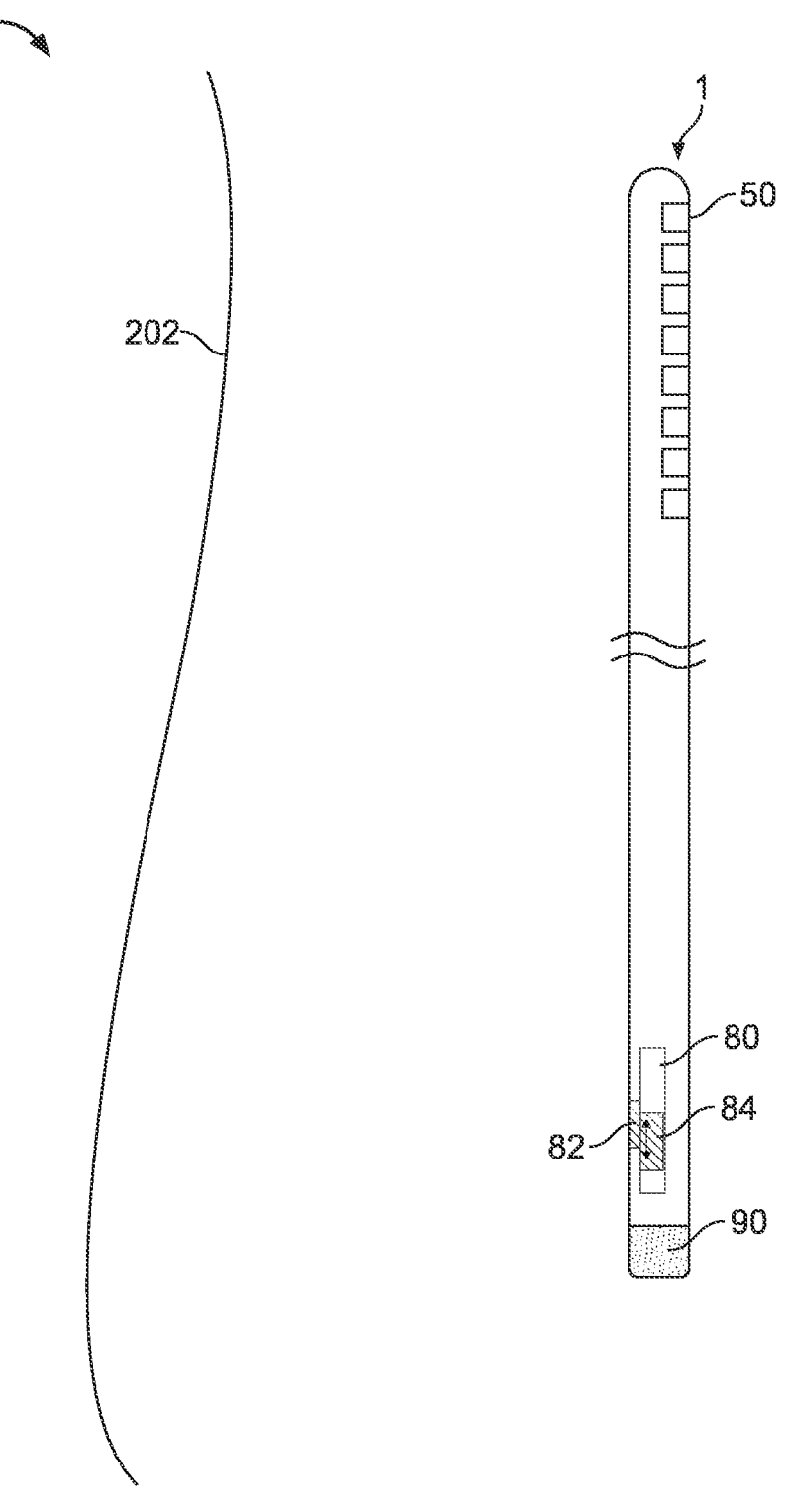
FIG. 7 illustrates a schematic view of a third means of powering of the collapsible neural stimulator, integrated into the lead of the stimulator.

Referring to FIGS. 5, 6, and 7, three schematic views of means of powering of the collapsible neural stimulator are shown.

In FIG. 5, the power and control unit 160 is fully internal. One or more piezoelectric generators 70, each including a cantilever arm 72 and weight 74, generate electricity for storage in the IPG 90. This power is carried to the collapsible neural stimulator 1 using a power transmission cable 92.

In FIG. 6, power is provided by a triboelectric generator 80. The motion of a first element 82 with respect to a second element 84 creates power for storage in the IPG 90, again carried to the collapsible neural stimulator 1 using a power transmission cable 92.

In FIG. 7, power is provided by a triboelectric generator 80, but the triboelectric generator 80 is now integrated into body of the collapsible neural stimulator 1. As before, the motion of a first element 82 with respect to a second element 84 creates power for storage in the IPG 90.

Figure 8:
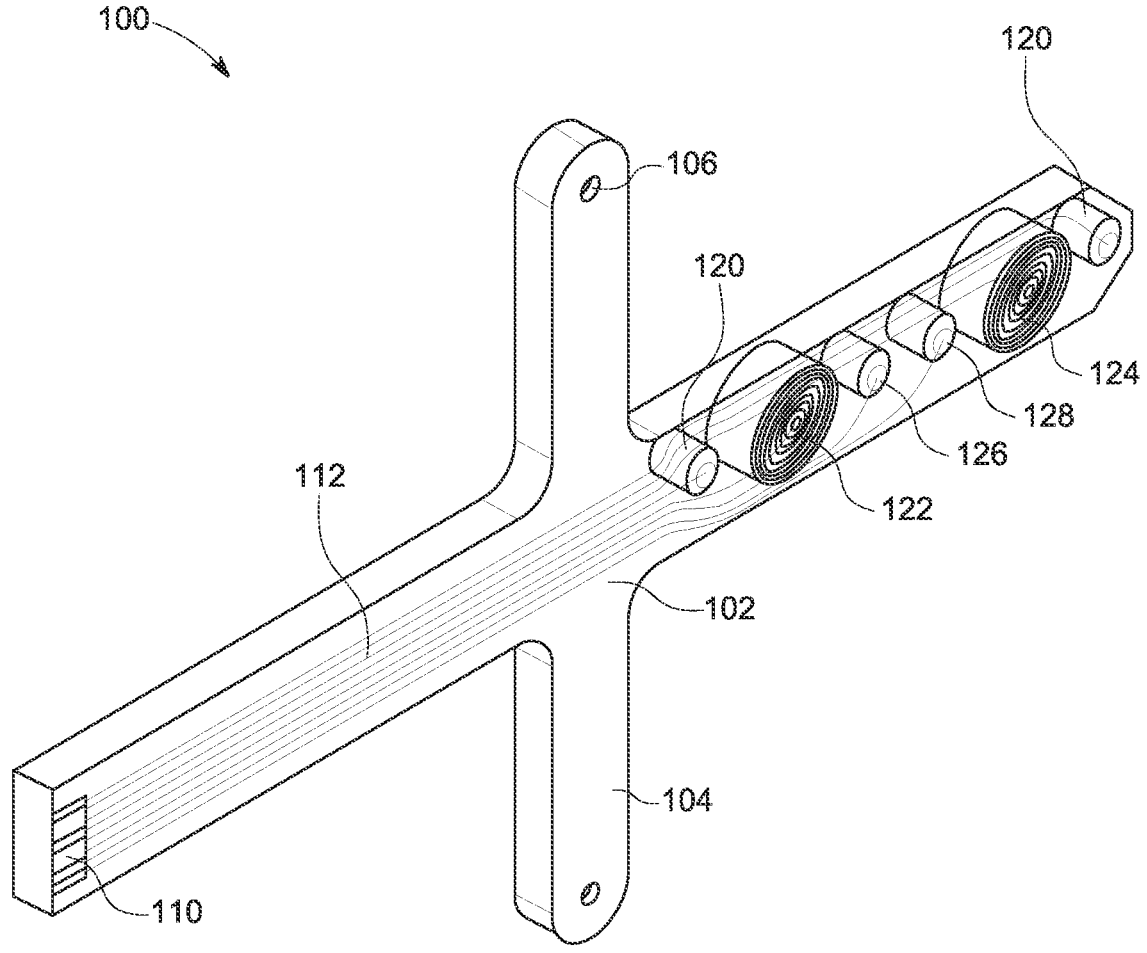
FIG. 8 illustrates a front isometric of an embodiment of the Closed-Loop Omnidirectional Neuromodulation with Eddy Currents (CLONE).
Figure 9:
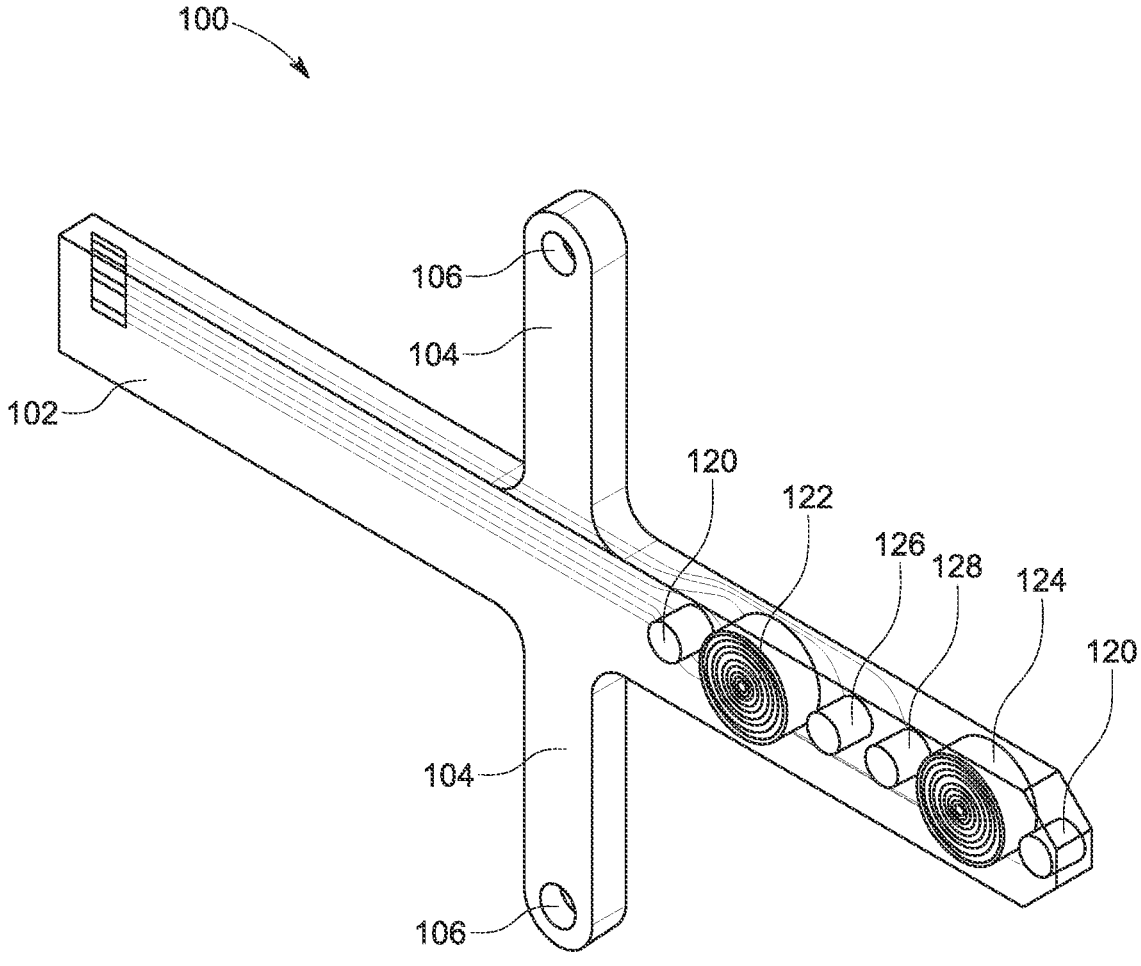
FIG. 9 illustrates a rear isometric of an embodiment Closed-Loop Omnidirectional Neuromodulation with Eddy Currents (CLONE).
Figure 10:
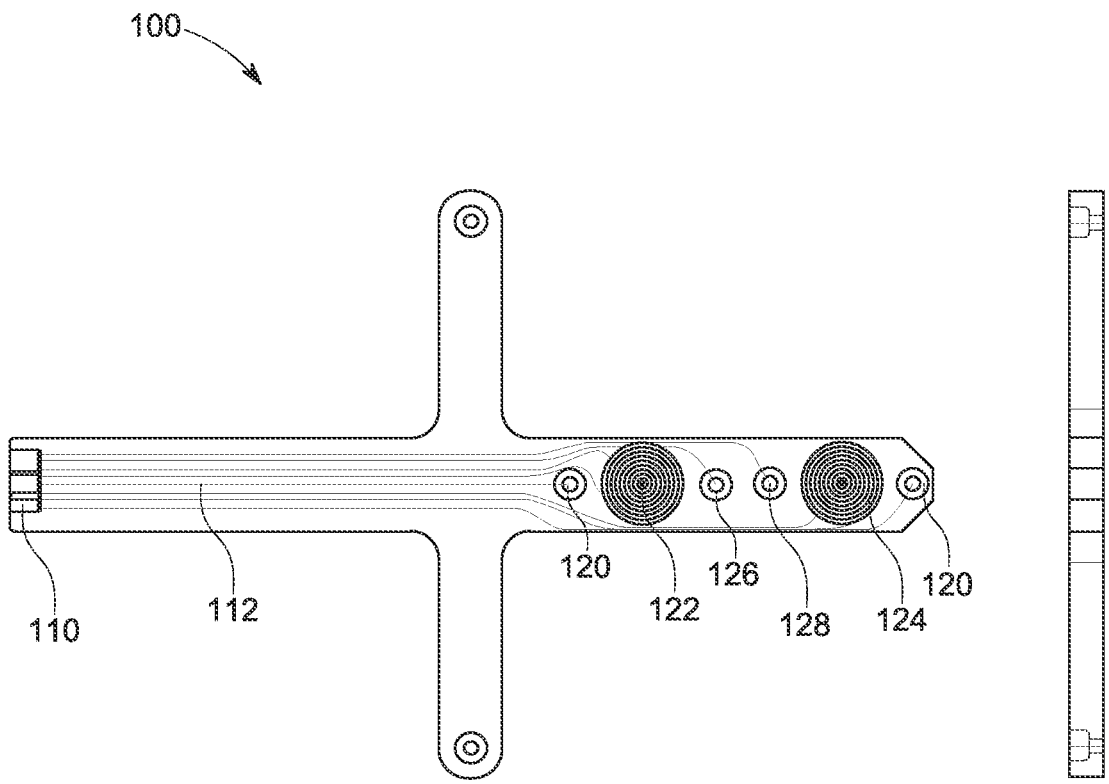
FIG. 10 illustrates a front view and side view of an embodiment of Closed-Loop Omnidirectional Neuromodulation with Eddy Currents (CLONE).

Referring to FIGS. 8 through 10, a second embodiment of the neural stimulator is shown.

The nerve stimulator 100 includes a body 102 with optional arms 104 that include suture holes 106.

The nerve stimulator 100 is connected to implantable pulse generator via the electrical contacts 110. The contacts no carry electrical signals to and from the nerve stimulator 100 across the array via wires 112.

The leads connect to the components of the nerve stimulator 100, including one or more recording/reference electrodes 120, a first magnetic planar coil 122, a second magnetic planar coil 124, an anode 126, and a cathode 128.

During operation, an implantable pulse generator causes the first magnetic planar coil 122 and the second magnetic planar coil 124 to emit magnetic signals, and the anode 126 and cathode 128 to emit electrical signals. The resulting evoked compound action potential is sensed by the recording/reference electrodes 120, which is reported back to the implantable pulse generator. The implantable pulse generator processes the resulting data, calculates a response, and issues a follow-up set of magnetic and electrical signals.

This process repeats as the implantable pulse generator continues to optimize signaling to result in the most-effective pain reduction while managing power consumption to conserve its power reserves.

Figure 11:
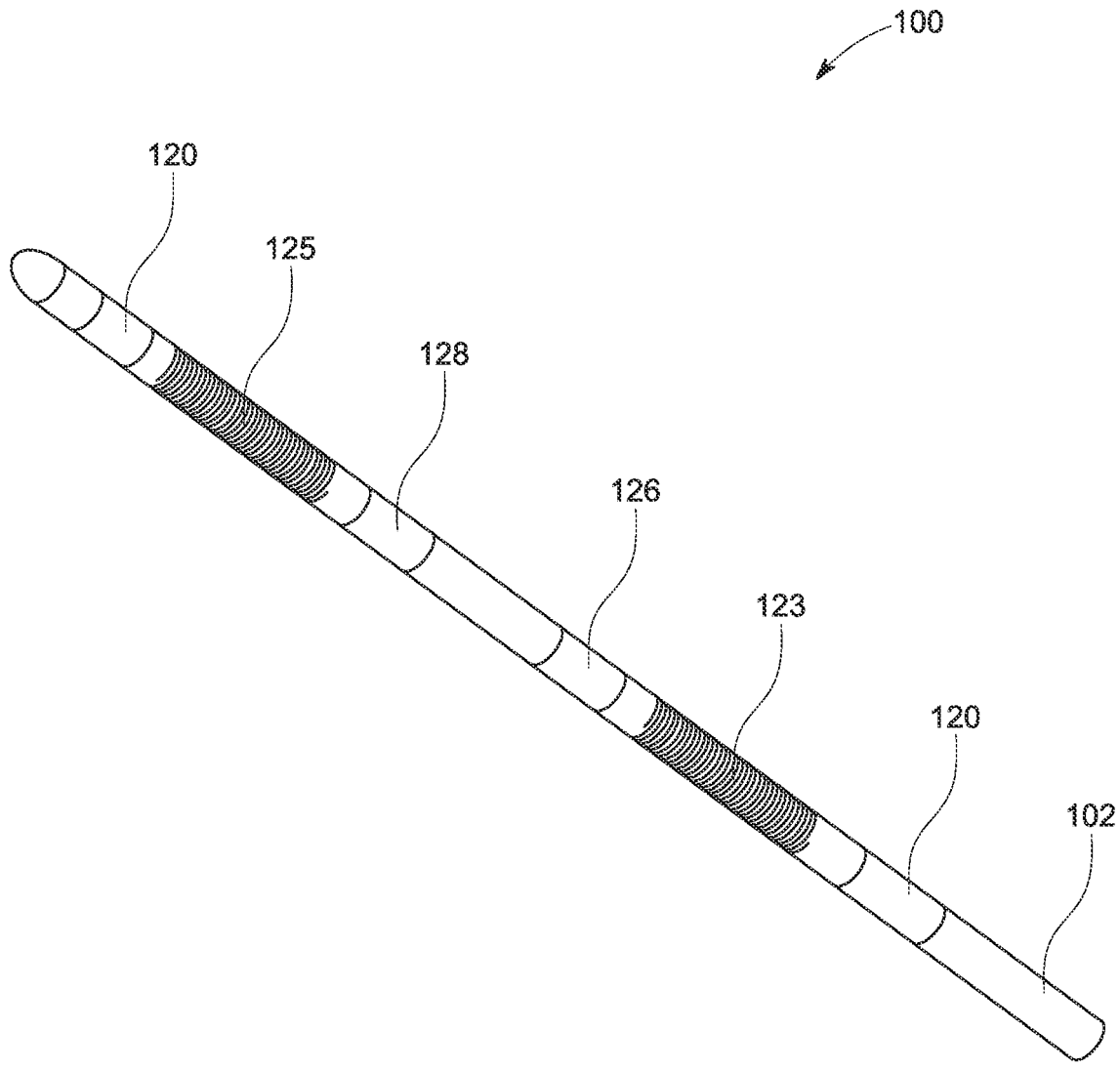
FIG. 11 illustrates an isometric of a cylindrical (isodiametric) embodiment of the Closed-Loop Omnidirectional Neuromodulation with Eddy Currents (CLONE).
Figure 12:
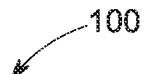
FIG. 12 illustrates a side view of a cylindrical (isodiametric) embodiment of the Closed-Loop Omnidirectional Neuromodulation with Eddy Currents (CLONE).
Figure 12:
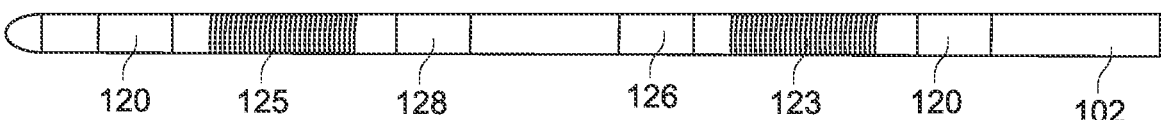

Referring to FIGS. 11 and 12, a cylindrical (isodiametric) embodiment of the collapsible neural stimulator is shown.

Again shown are a nerve stimulator 100 with body 102, recording/reference electrodes 120, a first magnetic cylindrical coil 123, a second magnetic cylindrical coil 125, an anode 126, and a cathode 128.

Figures 13A, 13B:
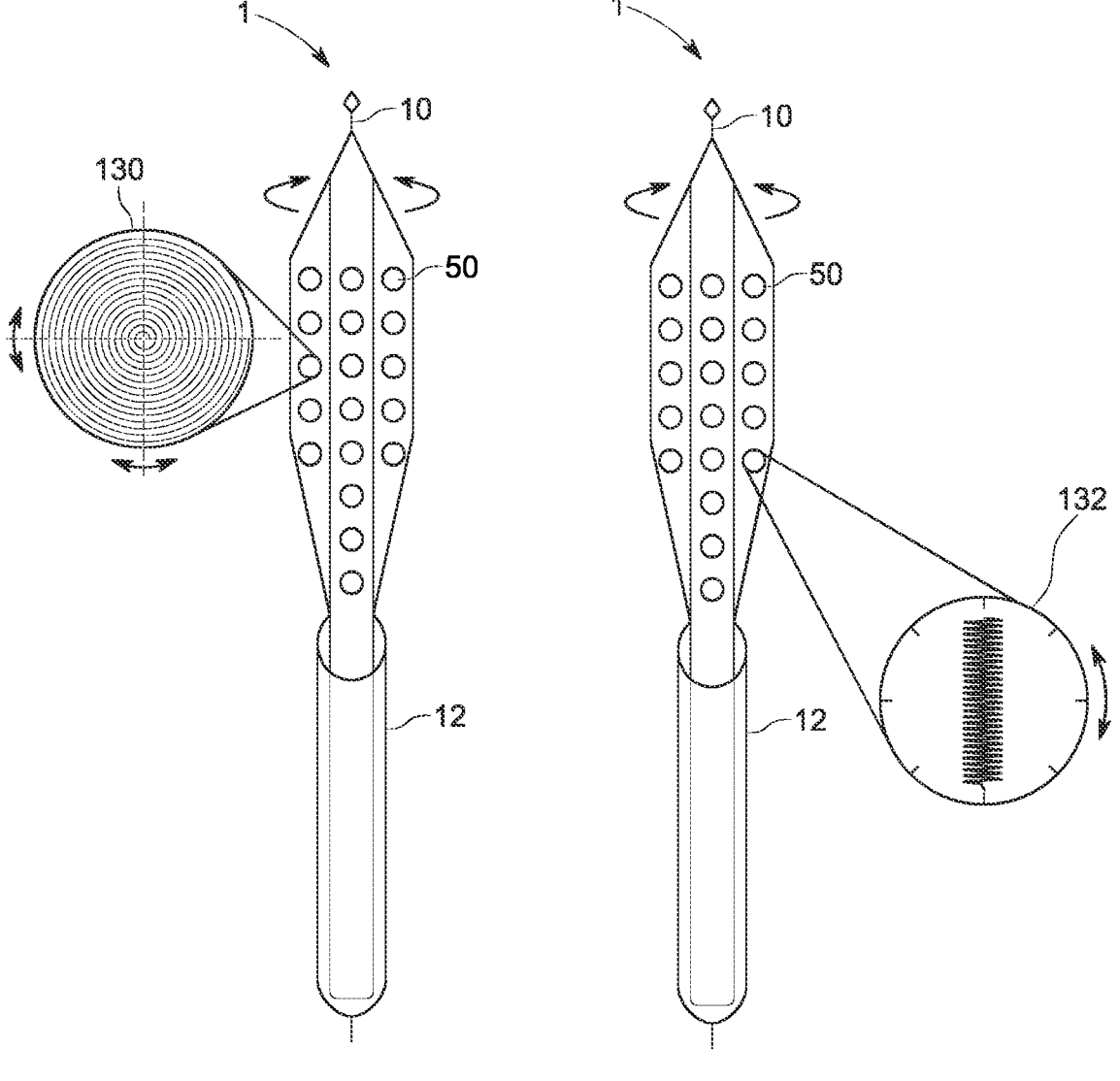
FIG. 13A illustrates a planar coil for use as an electrode.
FIG. 13B illustrates a cylindrical coil for use as an electrode.

Referring to FIGS. 13A and 13B, exemplary coils are shown. Embodiments of the electrodes 50 include planar coil 130 and cylindrical coil 132.

Planar coil 130 is housed within cylindrical disc placed at the location of an electrode 50. The planar coil 130 can tilt about one or more axes, allowing the planar coil 130 to be best positioned to steer the electrical or eddy currents. The result is neuro modulation between neurons—the neurons including nociceptive and neuropathic pain—ganglions, neurovasculature, and glial cells. Correctly positioning the planar coil 130 may be performed in conjunction with a 3D software program with epidural ultrasound above, postoperative imaging, or both.

Cylindrical coil 132 it is housed within its logical disk placed at the location of an electrode 50. The cylindrical coil 132 can rotate within its plane, allowing the cylindrical coil 132 to be best positioned to steer the electrical or eddy currents.

The result is neuro modulation between neurons—the neurons including nociceptive and neuropathic pain—ganglions, neurovasculature, and glial cells. Correctly positioning the planar coil 130 may be performed in conjunction with a 3D software program with epidural ultrasound above, postoperative imaging, or both.

Figure 14A:
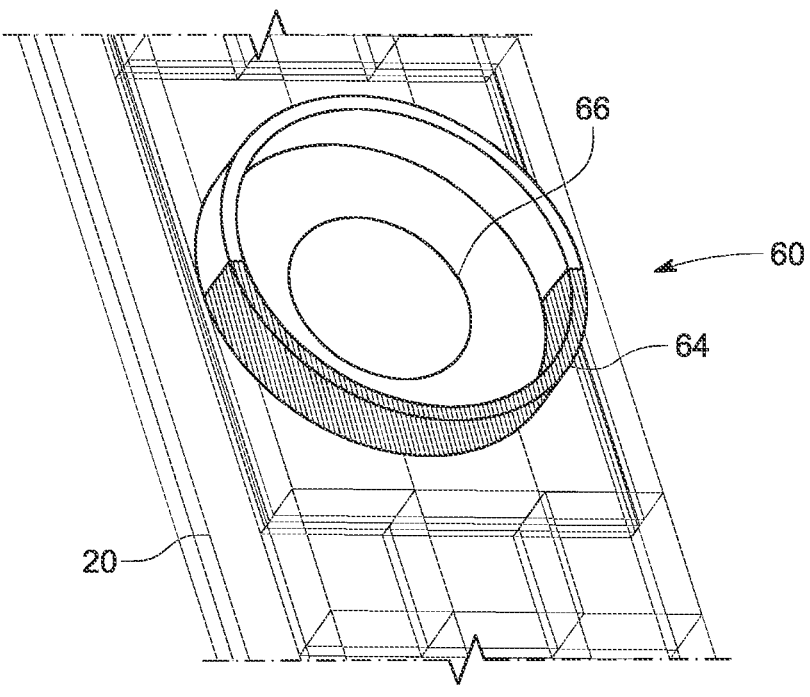
FIG. 14A illustrates a full-circle annular electrodes with an upper half activated.
Figure 14B:
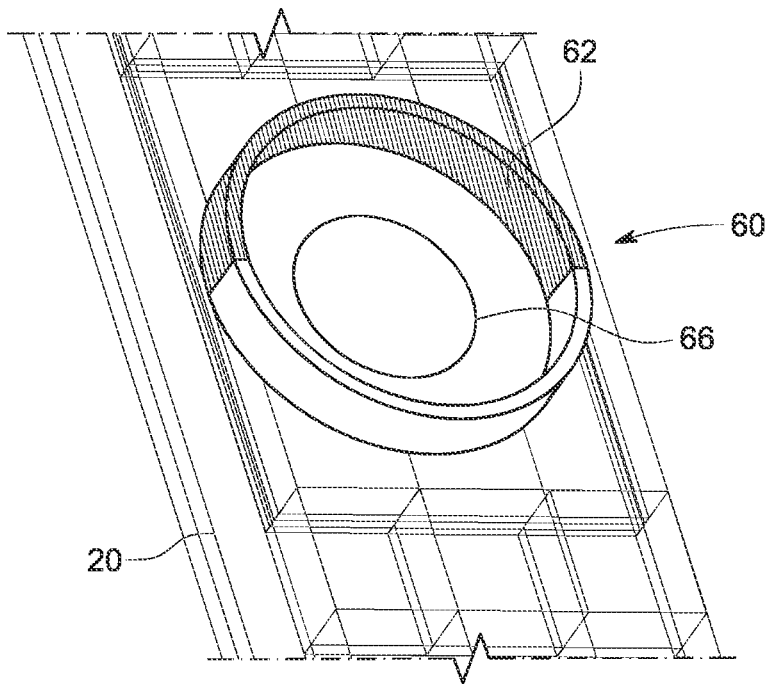
FIG. 14B illustrates a full-circle annular electrodes with a lower half activated.

FIGS. 14A and 14B illustrate a full-circle annular electrodes alternating between lower half activation and upper half activation.

Outer annular electrode 60 is shown alternating between outer annular electrode first segment 62 activation, FIG. 14B, and outer annular electrode second segment 64 activation, FIG. 14A.

Outer annular electrode 60 surrounds inner electrode 66.

The outer electrode 66 is segmented to create between 2 and 64 doublets, or between 1 and 32 pairs. Each individual electrode can act as either an anode or a cathode, steering the electrical current to the magnetic field peak. The timing of the electrical field and magnetic field pulses must coincide such that the combined effect of each subthreshold pulse will trigger an action potential.

The pairs of outer electrodes 60, in total, have the same surface area as the inner electrode 66. The charges are balanced due to the equivalent surface areas. Alternatively, the pairs of outer electrodes 60, in total, have a different surface area than inner electrode 66, and the difference in surface area is compensated for by varying the current. By increasing the charge applied to the smaller surface area, the electrode can balance its charge with a lesser current applied to a larger surface area. The higher surface charge density of the smaller surface area electrode can be restricted to not exceed a given desired or safety maximum, such as 30 μC/cm2.

Figure 15:
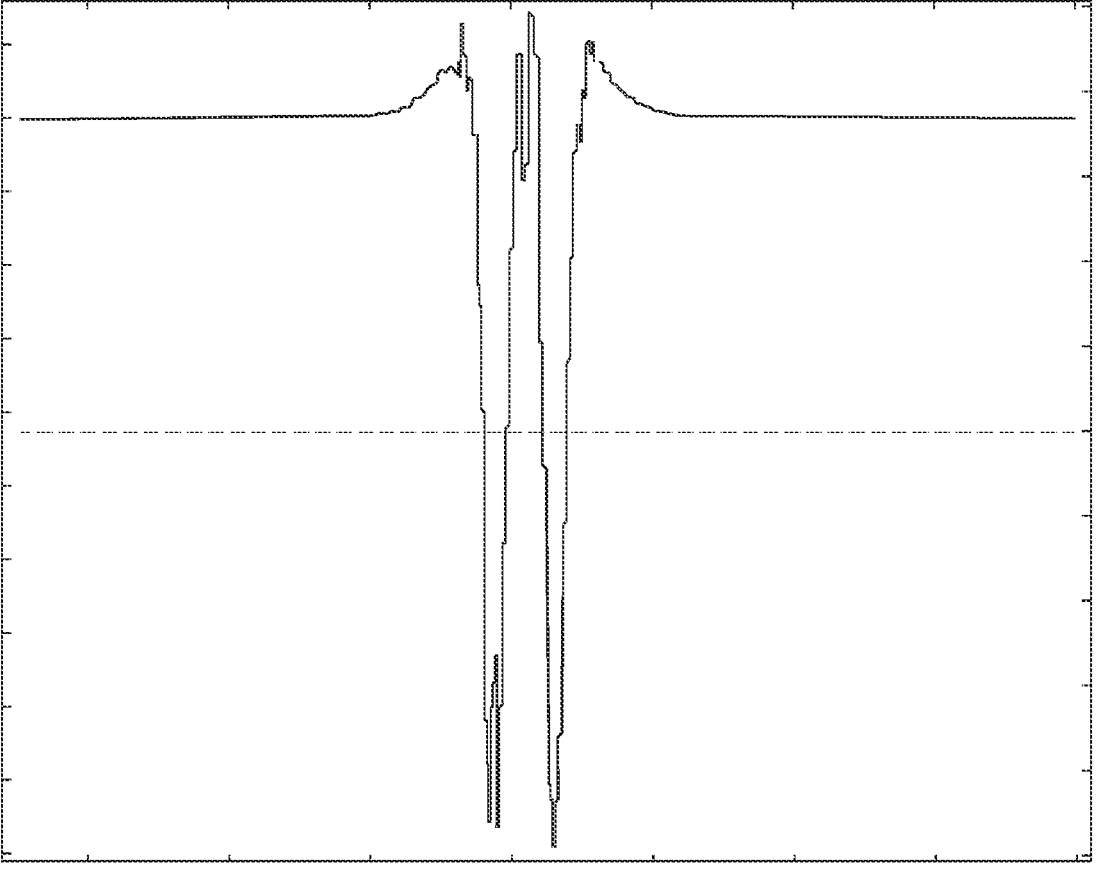
FIG. 15 illustrates a triple electrical peak.

FIG. 15 illustrates a triple electrical peak.

The electrical peaks between two annular electrodes—inner and outer—are further divided into a circular peak between the two electrodes, rather than a single linear peak with a linear electrode array; in a slice plot, the circular peak appears as three electrical peaks, providing a superior means to achieve more precise steering to coincide the electric field and magnetic field peaks.

Figure 16A:
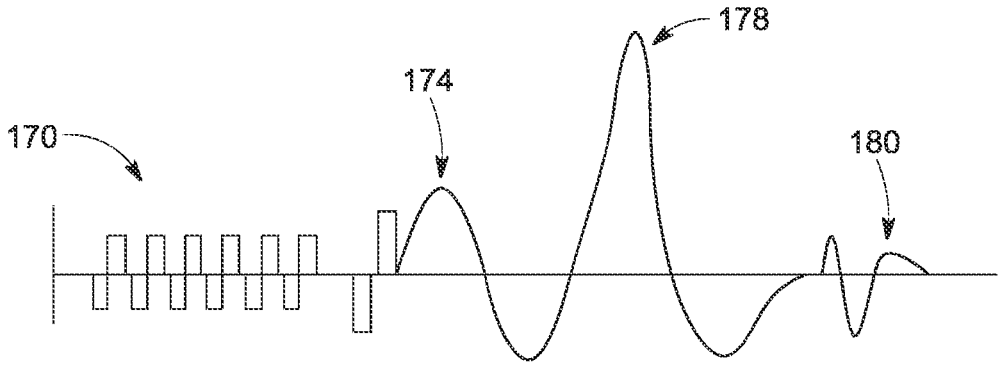
FIG. 16A illustrates it closed loop hybrid simulation showing optimal timing of electrical and magnetic pulses.

FIG. 16A illustrates it closed loop hybrid simulation showing optimal timing of electrical and magnetic pulses.

An electrical prime 170 is followed by a magnetic sine wave pulse 174, creating an action potential 178 and a magnetically induced ECAP 180.

Figure 16B:
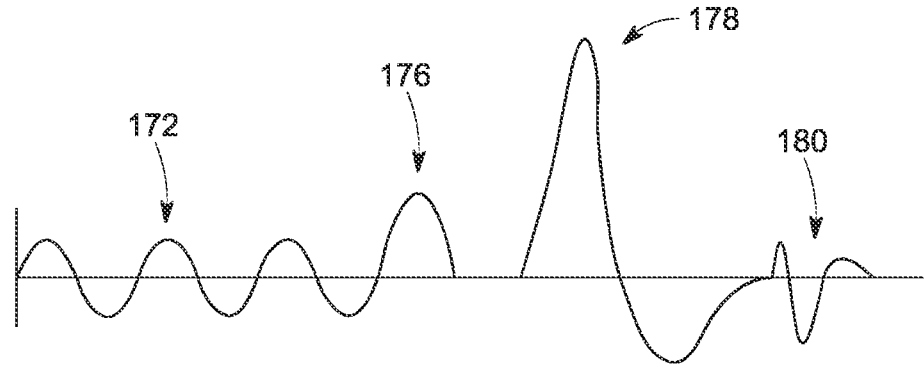
FIG. 16B shows closed loop hybrid simulation using only magnetic pulses.

FIG. 16B illustrates it closed loop hybrid simulation using only magnetic pulses.

The magnetic prime 172 is followed by a magnetic half sine wave pulse 176, creating an action potential 178 and a magnetically induced ECAP 180

Figure 17:
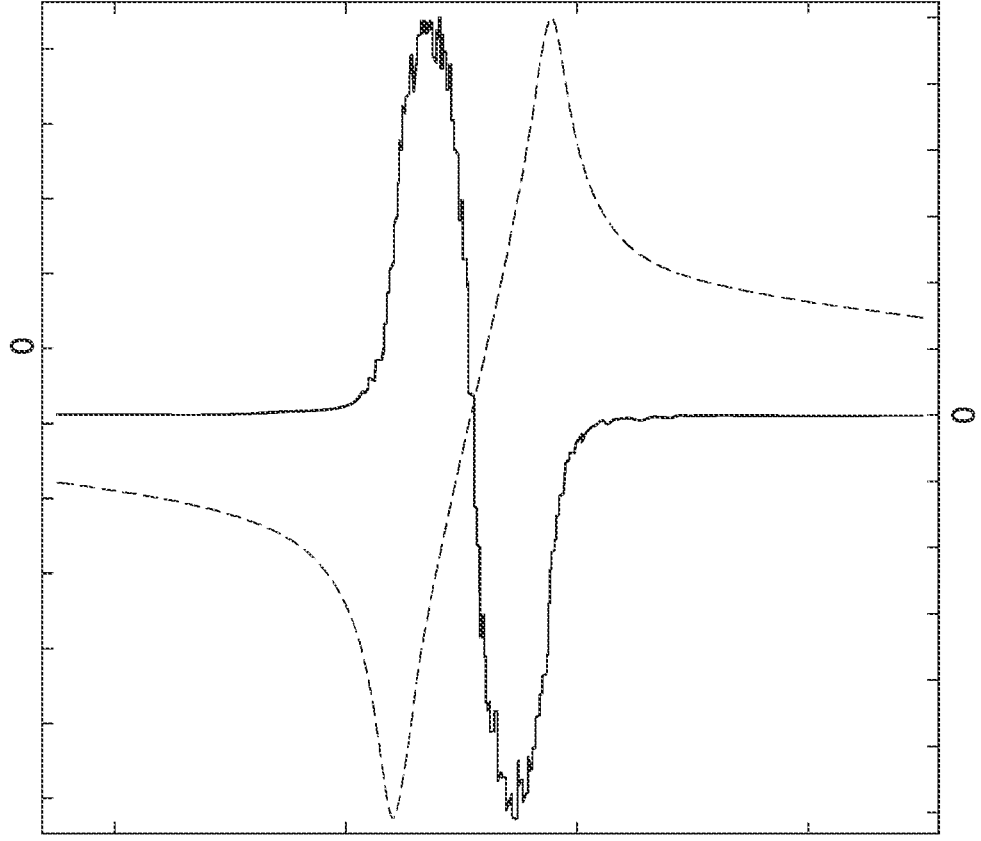
FIG. 17 shows coinciding electric and magnetic field peaks to obtain the desired complementary effect.

Referring to FIG. 17, coinciding electric and magnetic field peaks to obtain the desired complementary effect.

Modeling shows that the planar spiral produces a peak magnetic field of 3 mT at the center of the coil, reduced to 0.3 mT at the distance of the dorsal column.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof.

What is claimed is:

1. A method of modulating an interaction between neurons with a closed-loop stimulator using magnetically induced evoked compound action potentials, the neurons including ganglions, neurovasculature, and glial cells, by:
    exposing the neurons and the ganglions to a first signal;
        the first signal lowering a depolarization threshold of the neurons;
        the first signal having a first signal parameter;
    exposing the neurons and the ganglions to a second signal;
        the second signal causing depolarization, leading to down-regulation via neuromodulation, thus relieving nociceptive and neuropathic pain;
        the second signal having a second signal parameter;
    sensing magnetically induced evoked compound action potentials and late responses;
    measuring the magnetically induced evoked compound action potentials and the late responses;
    adjusting the first signal parameter to reduce the depolarization threshold;
    adjusting the second signal parameter to reduce depolarization;
    repeating the step of "exposing the neurons and ganglions to a first signal"; and
    repeating the step of "exposing the neurons and ganglions to a second signal";
    whereby exposing the neurons and the ganglions to the first signal lowers the depolarization threshold and the second signal causing the depolarization, thus relieving nociceptive and neuropathic pain.

2. The method of claim 1, where;
    the first signal parameter and the second signal parameter have a matching frequency, amplitude, phase polarity, relative phase, or harmonic content; or the first signal parameter and the second signal parameter have a different frequency, amplitude, phase polarity, relative phase, or harmonic content.

3. The method of claim 1, wherein the second signal is generated simultaneously with the first signal or the second signal is generated after the first signal has stopped.

4. The method of claim 1, wherein:

the first signal is a varying electrical field applied by an electrode or a set of annular electrodes; or the first signal is a constant electrical field applied by an electrode or a set of annular electrodes.

5. The method of claim 1, wherein the first signal is an electrical field having a frequency between 0.040 and 1500 Hz, with a pulse width between 4 to 1000 µs.

6. The method of claim 1, wherein the second signal is a magnetic field with a sinusoidal waveform, created by one or more planar coils, cylindrical coils, or inductors.

7. The method of claim 1, wherein the second signal is a magnetic field with a half sinusoidal waveform, also referred to as a full wave rectified sine wave, created by one or more planar coils, cylindrical coils, or inductors, resulting in increased energy efficiency.

8. The method of claim 1, wherein the second signal is:

a varying magnetic field created by one or more planar coils, cylindrical coils, or inductors; or a constant magnetic field created by one or more planar coils, cylindrical coils, or inductors.

9. A method of modulating an interaction between neurons—the neurons including nociceptors—ganglions, neurovasculature, and glial cells with a closed-loop stimulator by:

exposing the neurons and the ganglions to a magnetic signal;

the magnetic signal lowering a depolarization threshold of the neurons;

the magnetic signal having a magnetic signal parameter;

the magnetic signal generated by one or more planar coils, cylindrical coils, or inductors;

exposing the neurons and the ganglions to a second magnetic signal;

the second magnetic signal causing depolarization, leading to a down-regulation via neuromodulation, thus relieving a nociceptive and a neuropathic pain;

the second magnetic signal having a magnetic signal parameter;

sensing magnetically induced evoked compound action potentials (ECAP);

measuring the ECAP via strength duration curves, including measurements of Rheobases, Chronaxies, and Late Responses;

adjusting the magnetic signal parameter based on the measurements of Rheobases, Chronaxies, and Late Responses to reduce the depolarization;

adjusting the magnetic signal parameter based on the Rheobases and Chronaxies and Late Responses to reduce the depolarization leading to the down-regulation via neuromodulation, thus relieving the nociceptive and the neuropathic pain; and repeating the step of "exposing the neurons and ganglions to a magnetic signal";

whereby exposing the neurons and the ganglions to the magnetic signal to lower the depolarization threshold and a second magnetic signal causes depolarization causing a reduction in chronic pain.

10. The method of claim 9, wherein:

an initial sinusoidal magnetic pulse is followed by a second one-half sinusoidal pulsed magnetic signal, timed such that the second magnetic signal triggers an action potential and depolarization leading to down-regulation via neuromodulation, thus relieving nociceptive and neuropathic pain.

11. The method of claim 9, wherein the magnetic signal is generated simultaneously with the second magnetic signal or the second magnetic signal is generated after the magnetic signal has stopped.

12. The method of claim 9, wherein the step of "sensing a magnetically induced evoked compound action potentials" is performed by reference electrodes.

13. The method of claim 9, wherein the step of "sensing a magnetically induced evoked compound action potentials" is performed by a planar coil or cylindrical coil or inductor via induced electromotive force.

14. A neural stimulator for insertion into a nervous system of a patient, the neural stimulator comprising:

a lead;

the lead having a proximal portion and a distal portion; and the distal portion able to unfold and expand after insertion into the patient;

a planar coil, within the distal portion of the lead, is incorporated in a pseudoelastic memory metal or shape-memory polymer, the planar coil conforming to a structure in a central or peripheral nervous system to provide more effective neuromodulation; or a cylindrical coil, within the distal portion of the lead, is incorporated in a pseudoelastic memory metal or shape-memory polymer, the cylindrical coil conforming to the structure in a central or peripheral nervous system to provide more effective neuromodulation, whereby the unfolded distal portion is wider than the proximal portion, thus permitting insertion of a lead that unfolds to a greater size than able to be directly inserted.

15. The neural stimulator for insertion into nervous system of a patient of claim 14 wherein;

the lead is constructed of a biologically compatible material that causes the lead to unfold when the lead is warmed by body heat from the patient;

whereby the lead automatically unfolds, reducing a number of steps that a surgeon must take to place the lead.

16. The neural stimulator for insertion into nervous system of a patient of claim 15, further comprising:

two or more magnets that interact to hold a first medial portion of the lead to a second medial portion of a second lead as a means to increase a strength of a magnetic field.

17. The neural stimulator for insertion into nervous system of a patient of claim 14, further comprising:

a circular disc housing the planar coil or the cylindrical coil;

wherein when the planar coil is within the circular disc, the circular disc tilts on one axis or several different axes, thus allowing the neural stimulator to steer electrical or eddy currents providing a neuromodulation effect; and wherein when the cylindrical coil is within the circular disc, the circular disc can rotate between 0 to 360 degrees, thus allowing the neural stimulator to steer electrical or eddy currents providing a neuromodulation effect.

18. The neural stimulator for insertion into nervous system of a patient of claim 14, further comprising:

an implantable pulse generator connected to the lead.

19. The neural stimulator for insertion into nervous system of a patient of claim 14, further comprising:

a nanogenerator that functions as an implantable pulse generator;

the nanogenerator converting kinetic energy into electrical energy;

the electrical energy used to charge the lead.

\* \* \* \* \*